United States Patent
Severns et al.

(10) Patent No.: US 10,064,647 B2
(45) Date of Patent: Sep. 4, 2018

(54) SCALPEL BLADE REMOVER

(71) Applicant: Aspen Surgical Products, Inc., Caledonia, MI (US)

(72) Inventors: Ryan Severns, Plainwell, MI (US); Murray Swoish, Caledonia, MI (US)

(73) Assignee: Aspen Surgical Products, Inc., Caledonia, MI (US)

( * ) Notice: Subject to any disclaimer, the term of this patent is extended or adjusted under 35 U.S.C. 154(b) by 269 days.

(21) Appl. No.: 14/879,391

(22) Filed: Oct. 9, 2015

(65) Prior Publication Data

US 2017/0100151 A1    Apr. 13, 2017

(51) Int. Cl.
*B65D 83/10* (2006.01)
*A61B 17/3217* (2006.01)

(52) U.S. Cl.
CPC ..... *A61B 17/3217* (2013.01); *Y10T 29/53683* (2015.01); *Y10T 29/53943* (2015.01)

(58) Field of Classification Search
CPC ........... A61B 17/3217; Y10T 29/53683; Y10T 29/53943
USPC ....... 206/352, 354, 355, 359; 29/426.6, 239, 29/278; 30/162; 606/167
See application file for complete search history.

(56) References Cited

U.S. PATENT DOCUMENTS

| | | | |
|---|---|---|---|
| 4,120,397 A | 10/1978 | Neumann | |
| 4,168,777 A | 9/1979 | Gaskell et al. | |
| 4,180,162 A | 12/1979 | Magney | |
| 4,270,416 A | 6/1981 | Thompson | |
| 4,318,473 A | 3/1982 | Sandel | |
| 4,386,457 A | 6/1983 | Coombs | |
| 4,395,807 A | 8/1983 | Eldridge, Jr. et al. | |
| 4,466,539 A | 8/1984 | Frauenhoffer | |
| 4,730,376 A | 3/1988 | Yamada | |
| 4,746,016 A | 5/1988 | Pollak et al. | |
| 4,903,390 A | 2/1990 | Vidal et al. | |
| 4,998,334 A * | 3/1991 | Pemberton | A61B 17/3217 206/359 |
| D319,873 S | 9/1991 | Rouse | |
| 5,088,173 A | 2/1992 | Kromer et al. | |
| D328,026 S | 7/1992 | Stenstrom | |
| 5,163,553 A | 11/1992 | Cantwell et al. | |

(Continued)

FOREIGN PATENT DOCUMENTS

| | | |
|---|---|---|
| EP | 2915495 A1 | 9/2015 |
| WO | 2004093706 A1 | 11/2004 |

OTHER PUBLICATIONS

European Search Report from corresponding Application No. 16192695.1-1659 dated Dec. 19, 2016.

*Primary Examiner* — Luan K Bui
(74) *Attorney, Agent, or Firm* — Price Heneveld LLP

(57) ABSTRACT

A blade disarmer is provided herein. The blade disarmer includes a base member having an elongated portion, a bottom portion, and first and second walls extending from the elongated portion. A cover member is removably attached to the base member forming a cavity therebetween. The cover member includes a hinge separating a body portion and a tab. A pair of dome-shaped portions is disposed on the tab configured to assist a pair of side surfaces of the tab proximate each respective dome-shaped portion to flex laterally. A closure mechanism is disposed on the first and second walls and configured to maintain the tab in a plurality of positions. First and second protrusions extend into the cavity.

19 Claims, 28 Drawing Sheets

(56) References Cited

U.S. PATENT DOCUMENTS

| | | | |
|---|---|---|---|
| 5,301,807 A * | 4/1994 | Donahue | A45C 11/24 206/363 |
| D349,204 S | 8/1994 | Lefebvre | |
| 5,449,068 A | 9/1995 | Gharibian | |
| D366,527 S | 1/1996 | Paterson | |
| D372,782 S | 8/1996 | Spehalski | |
| 5,660,299 A * | 8/1997 | Harvey | A45C 11/20 220/254.3 |
| 5,662,221 A | 9/1997 | Abidin et al. | |
| 5,667,067 A | 9/1997 | Gabriel | |
| 5,699,908 A | 12/1997 | Frye et al. | |
| 5,706,942 A | 1/1998 | Vila et al. | |
| 5,729,879 A | 3/1998 | Hoftman | |
| 5,868,771 A * | 2/1999 | Herbert | A61B 17/3213 30/162 |
| 5,875,532 A * | 3/1999 | Musgrave | A61B 17/3215 206/355 |
| 5,875,533 A | 3/1999 | Henry | |
| 5,938,027 A | 8/1999 | Soroff et al. | |
| 6,216,868 B1 | 4/2001 | Rastegar et al. | |
| 7,036,660 B1 | 5/2006 | Abidin et al. | |
| 7,155,795 B2 | 1/2007 | Abidin et al. | |
| 7,207,999 B2 * | 4/2007 | Griffin | A61B 17/3213 606/167 |
| 7,398,880 B2 * | 7/2008 | Henry | A61B 17/3217 206/355 |
| D583,821 S | 12/2008 | Richter | |
| D703,626 S | 4/2014 | Hermansen | |
| 2007/0039844 A1 | 2/2007 | Zyzelewski et al. | |

\* cited by examiner

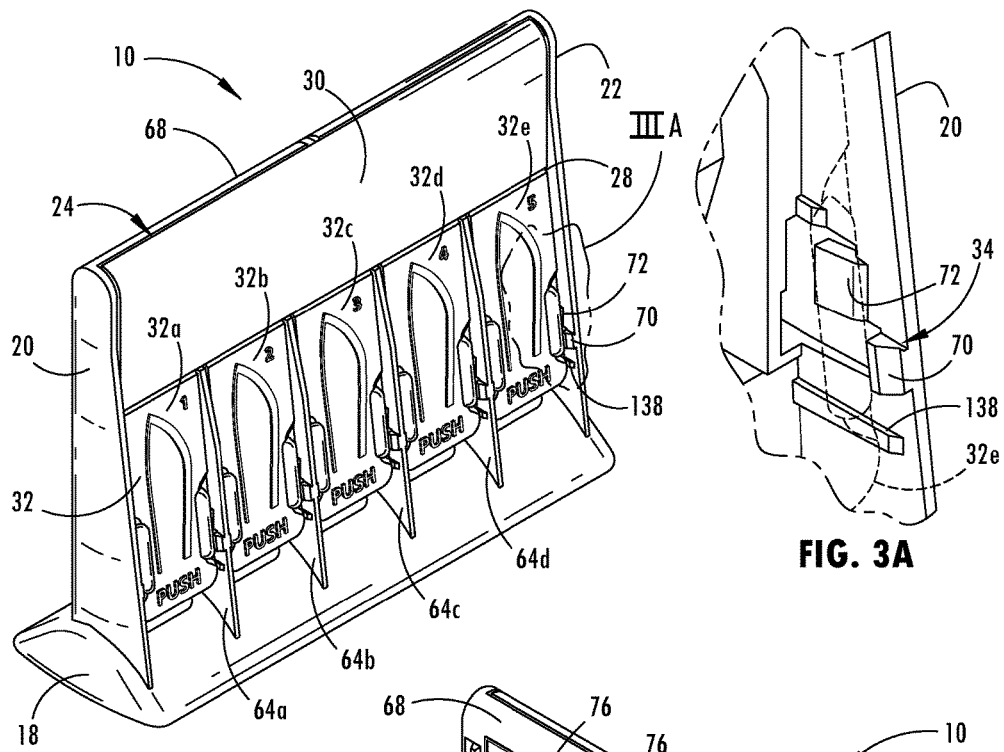
FIG. 3
FIG. 3A
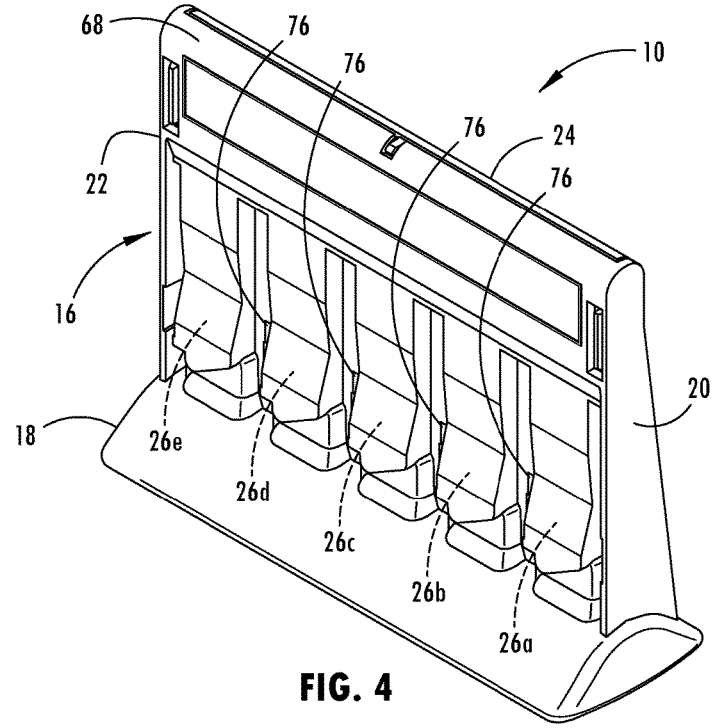
FIG. 4

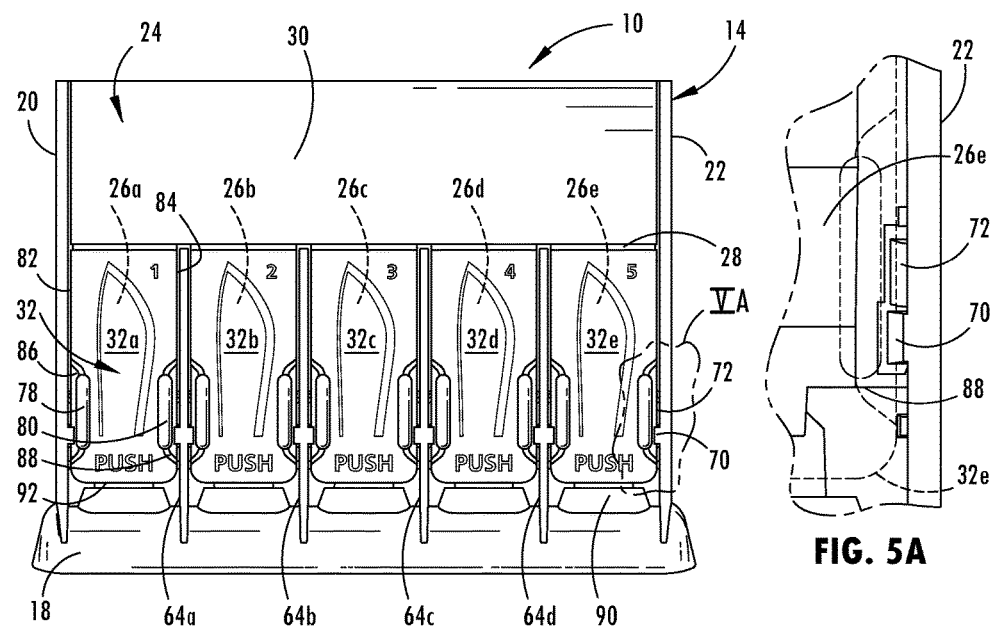
FIG. 5
FIG. 5A
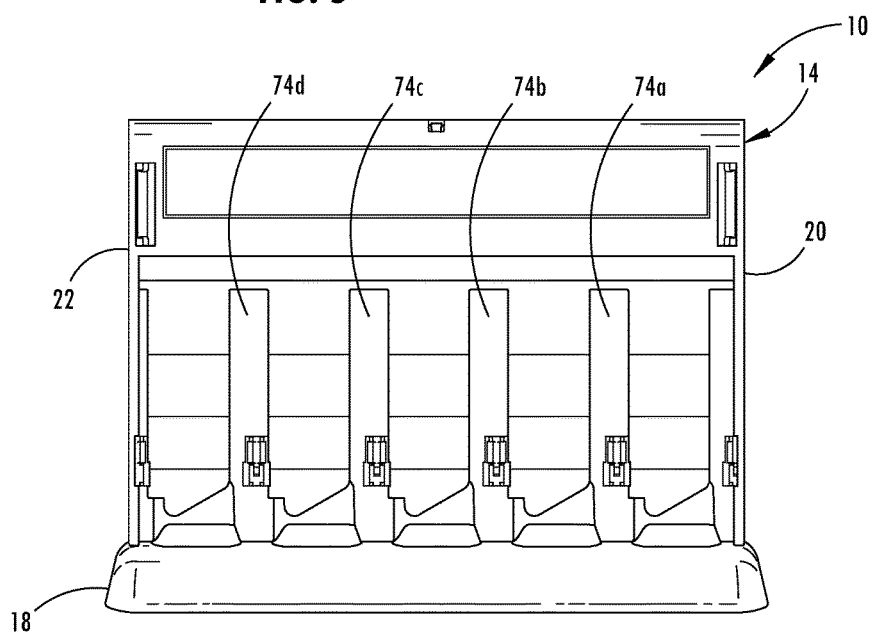
FIG. 6

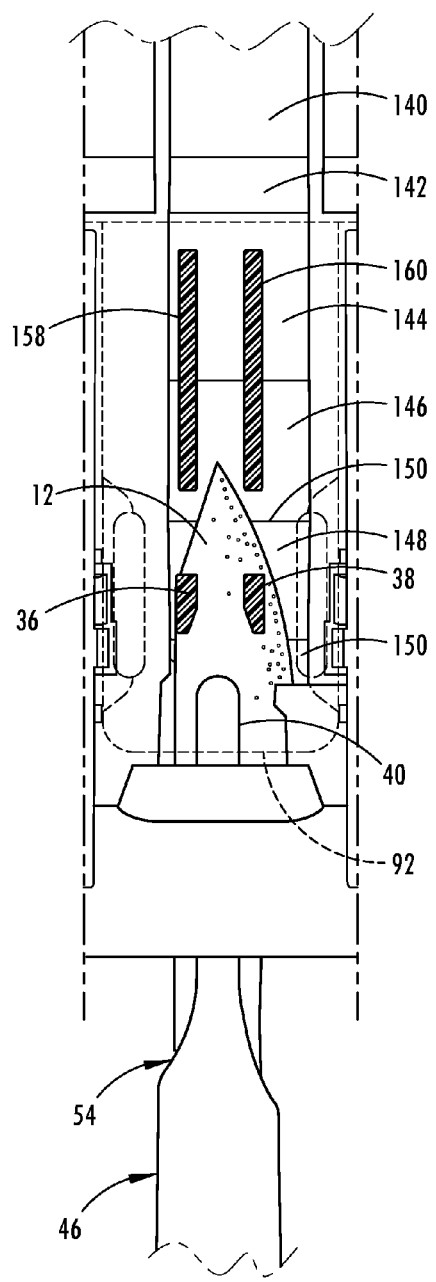
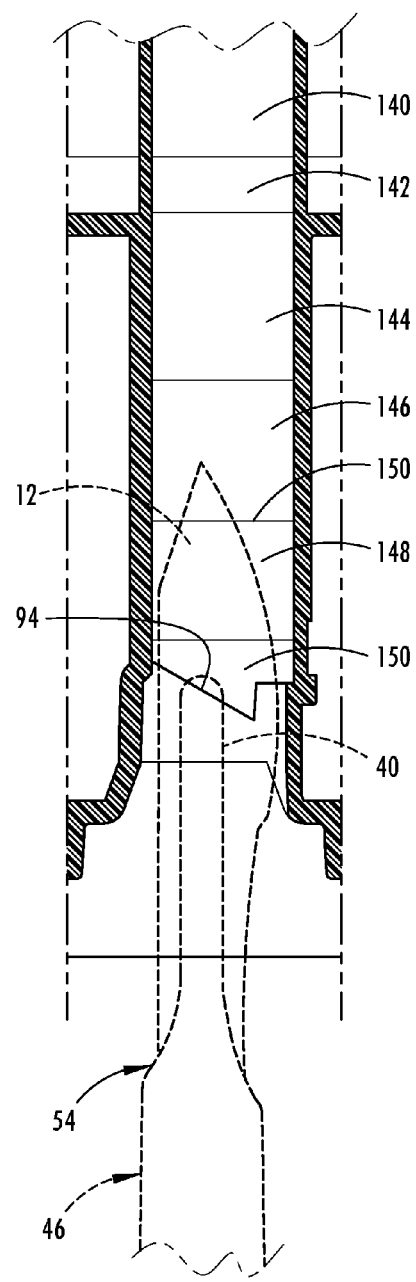
FIG. 24C
FIG. 24D

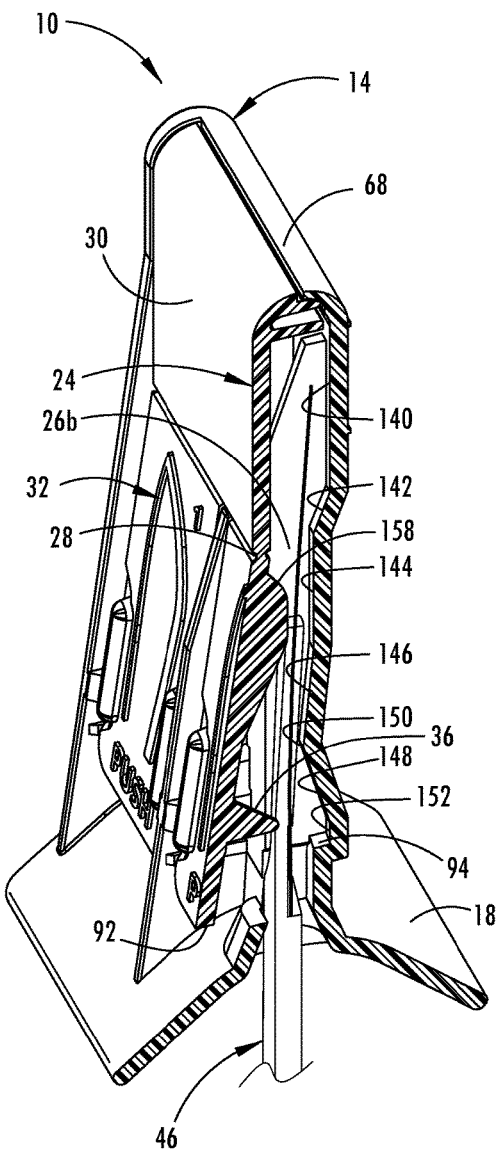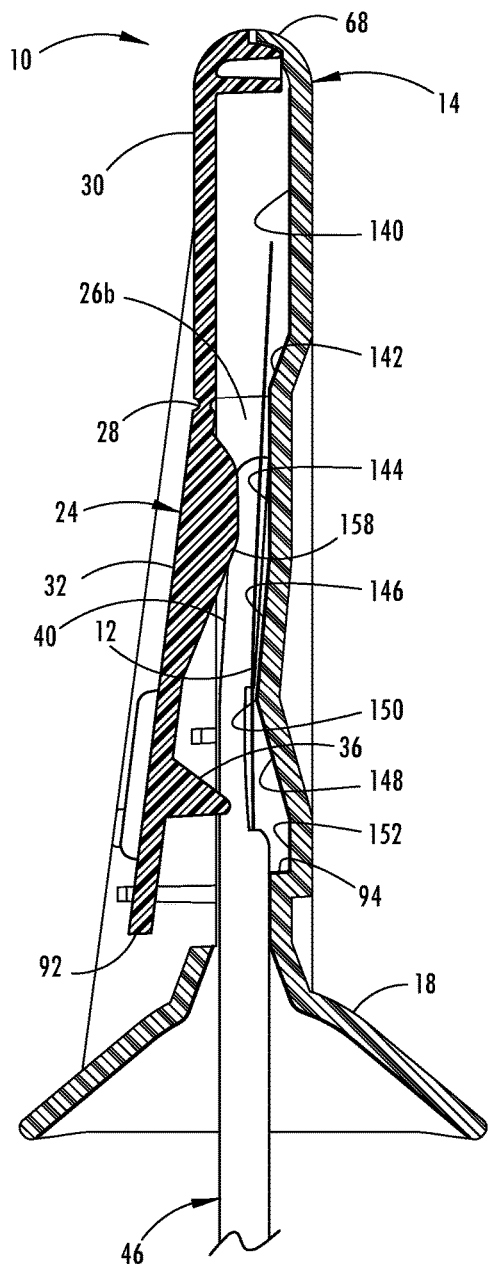
FIG. 25A  FIG. 25B

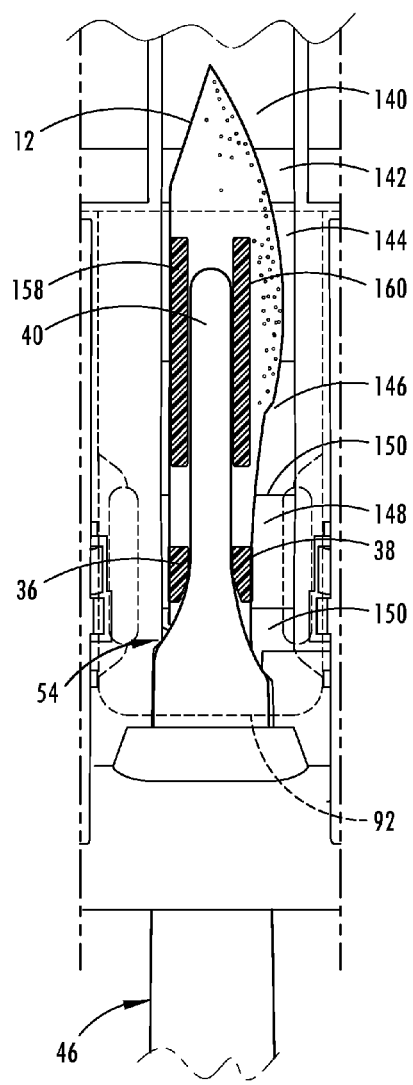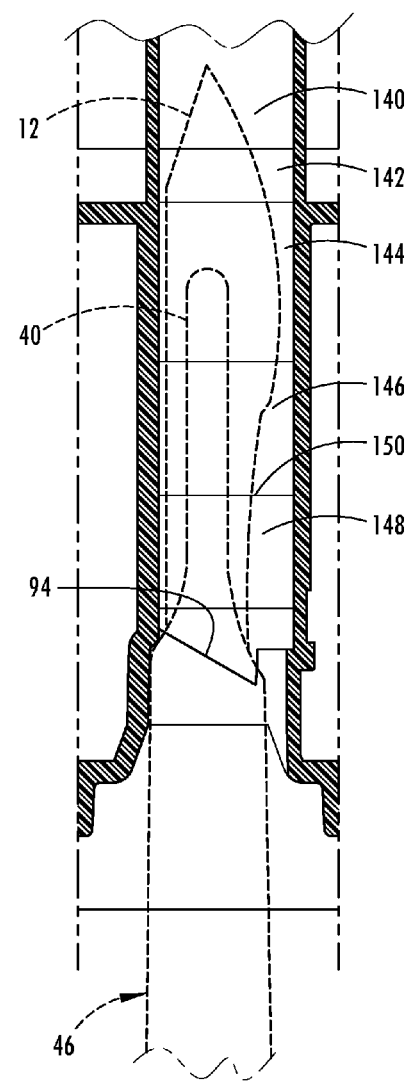
FIG. 25C  FIG. 25D

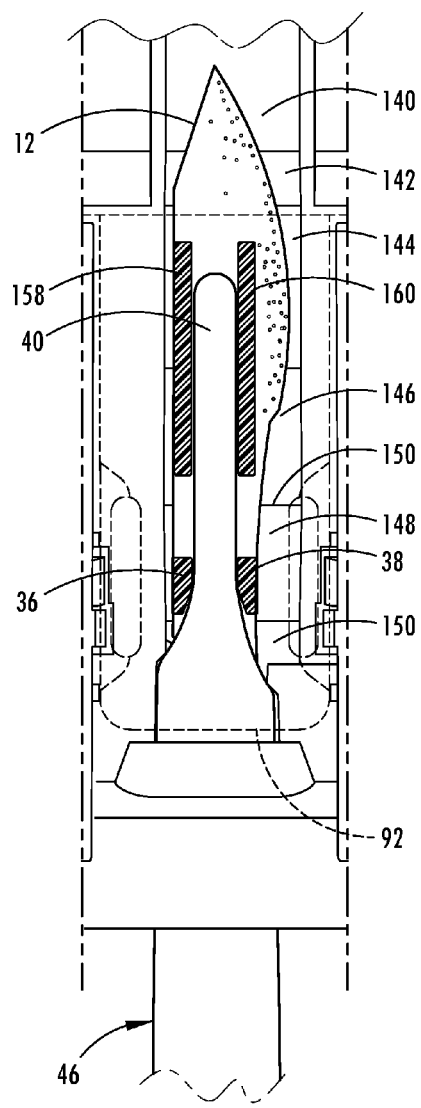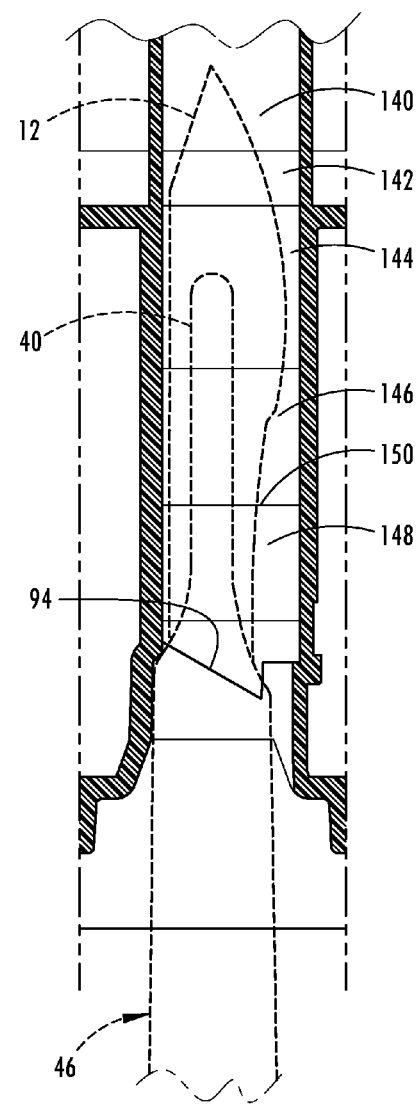
FIG. 26C  FIG. 26D

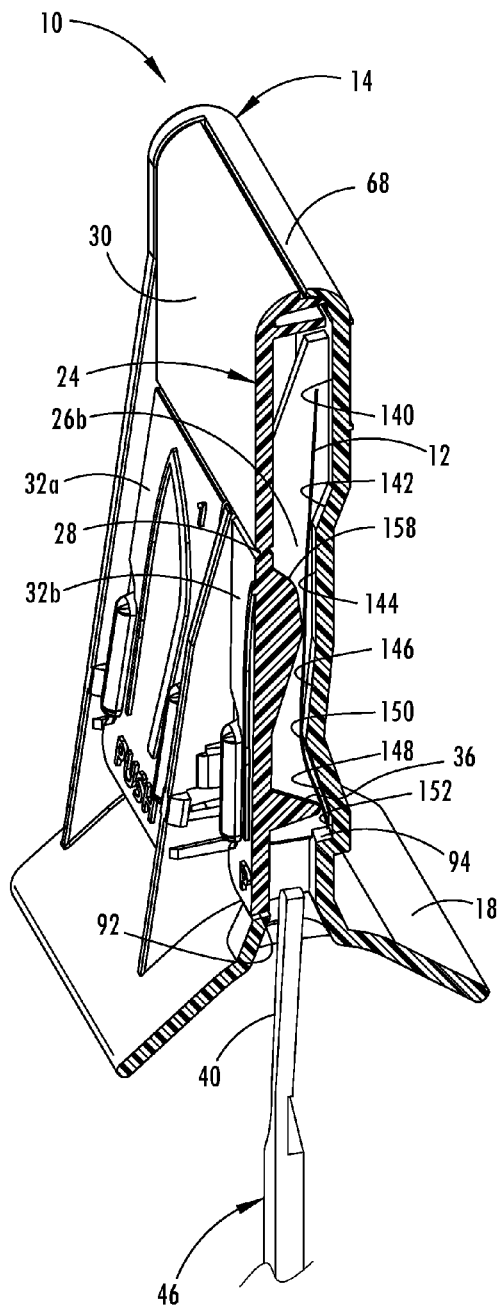
FIG. 27A  FIG. 27B

US 10,064,647 B2

SCALPEL BLADE REMOVER

TECHNOLOGICAL FIELD

The present disclosure relates generally to a container for medical blades. In particular, the blade disarmer removes a blade from a medical tool and retains the blade in a substantially enclosed blade disarmer.

BACKGROUND

Accidental cuts or punctures may occur due to blade instruments, either during use, during transfer from one person to another, or from inadvertent misplacement thereof in potentially dangerous locations. In particular, scalpels may include a reusable handle that can be assembled with a disposable blade. Such handles may not include any protection from contact with the blade when assembled thereto and, further, may present additional opportunity for injury during removal of a to-be-disposed blade prior to reuse of the handle. Accordingly, further advances in protection from injury due to inadvertent contact with scalpel blades, including during removal and dispensing of the blades, are desired.

SUMMARY

According to one aspect of the disclosure, a blade disarmer is disclosed. The blade disarmer includes a base member having an elongated portion, a bottom portion, and first and second walls extending from the elongated portion. A cover member is removably attached to the base member forming a cavity therebetween. The cover member includes a hinge separating a body portion and a tab. A pair of dome-shaped portions is disposed on the tab configured to assist a pair of side surfaces of the tab proximate each respective dome-shaped portion to flex laterally. A closure mechanism is disposed on the walls and configured to maintain the tab in a plurality of positions. First and second protrusions extend into the cavity and are configured to contact a blade within the cavity.

According to another aspect of the disclosure, a blade disarmer is disclosed. The blade disarmer includes a base member having an elongated portion, a bottom portion, and a plurality of walls extending from the elongated portion. A cover member having a body portion is removably attached to the base member forming a cavity there between. A plurality of tabs is pivotably coupled to the body portion. First and second detents are disposed on the plurality of walls and extend away from each wall. The first detent is disposed at a first distance from the elongated portion and the second detent is disposed at a second distance from the elongated portion.

According to another aspect of the disclosure, a method for removing a blade within a blade disarmer is disclosed. The method includes forming a cavity between a base member and cover member. A scalpel handle with a blade attached thereto is then inserted into the cavity. A shoulder portion of the scalpel is paired to a shoulder mating portion within the cavity. A tab on a cover member is pressed thereby rotating the tab from a first position to a second position. A pair of protrusions are pressed against a distal heel portion of the blade. The blade is then bent out of a planar orientation as a pair of elongate ribs maintain a predefined position of a proximal cutting portion of the blade thereby bending the blade about an apex. The scalpel handle is removed from an insertion opening with the blade maintaining a bent position within the cavity.

These and other features, advantages, and objects of the present device will be further understood and appreciated by those skilled in the art upon studying the following specification, claims, and appended drawings.

BRIEF DESCRIPTION OF THE DRAWINGS

In the drawings:

FIG. 3 is a front top perspective view of the blade disarmer formed from a base member attached to a cover member;

FIG. 3A is an enlarged perspective view of area IIIA of FIG. 3 with a portion of the cover member in phantom;

FIG. 4 is a rear top perspective view of the blade disarmer;

FIG. 5 is a front elevational view of the blade disarmer;

FIG. 5A is an enlarged elevational view of area VA of FIG. 5 with a portion of the cover member in phantom;

FIG. 6 is a rear elevational view of the blade disarmer;

FIG. 24C is a partial front elevational view of a blade partially inserted into the cavity with a portion of the cover in phantom;

FIG. 24D is a partial front elevational view of a blade partially inserted into the cavity with the blade and scalpel in phantom;

FIG. 25A is a front perspective cross-sectional view taken along XXVA-XXVA of FIG. 25 illustrating the blade disarmer having the blade fully inserted into the cavity formed between the base member and the cover member;

FIG. 25B is a side elevational cross-sectional view taken along the line XXVA-XXVA of FIG. 25 illustrating the blade fully inserted into the cavity;

FIG. 25C is a partial front elevational view of the blade fully inserted into the cavity with a portion of the cover member in phantom;

FIG. 25D is a partial front elevational view of the blade fully inserted into the cavity with the blade and scalpel in phantom;

FIG. 26C is a partial front elevational view of a blade fully inserted into the cavity and the tab rotated from a first position to a second position with a portion of the cover member in phantom;

FIG. 26D is a partial front elevational view of the tab in the second position with the blade and scalpel in phantom;

FIG. 27A is a front perspective cross-sectional view taken along XXVIIA-XXVIIA of FIG. 27 illustrating the scalpel handle removed from the blade disarmer and the blade disposed with the cavity;

FIG. 27B is a front perspective cross-sectional view taken along XXVIIA-XXVIIA of FIG. 27 illustrating the scalpel handle removed from the blade disarmer and the blade disposed with the cavity;

DETAILED DESCRIPTION OF EMBODIMENTS

Figure 1:
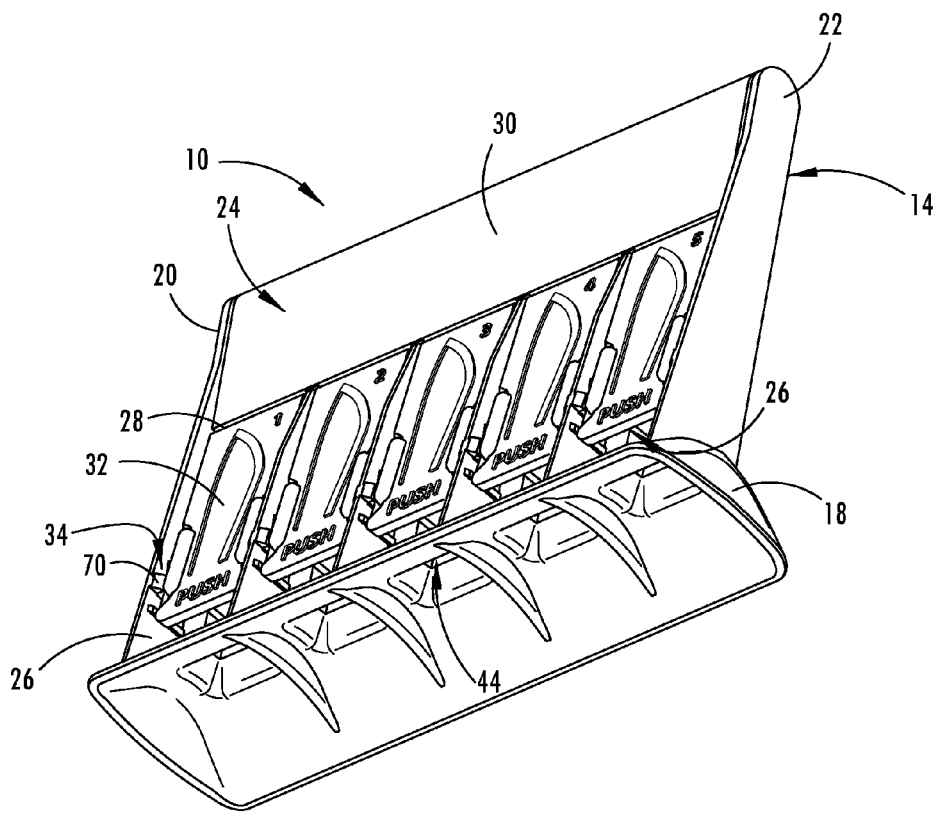
FIG. 1 is a bottom perspective view of one embodiment of a blade disarmer of the present disclosure.

For purposes of description herein, the terms "upper," "lower," "right," "left," "rear," "front," "vertical," "horizontal," and derivatives thereof shall relate to the disclosure as oriented in FIG. 3. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As required, detailed embodiments of the present disclosure are disclosed herein. However, it is to be understood that the disclosed embodiments are merely exemplary of the disclosure that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Referring to FIGS. 1-33, reference numeral 10 generally designates a blade disarmer that is configured to remove and retain a blade 12. The blade disarmer 10 includes a base member 14 having an elongated portion 16, a bottom portion 18, and first and second exterior walls 20, 22 extending from the elongated portion 16. A cover member 24 is removably attached to the base member 14 forming a cavity 26 therebetween. The cover member 24 includes a hinge 28 that separates a body portion 30 and a tab 32. A pair of dome-shaped portions 78, 80 are disposed on the tab 32. The pair of dome-shaped portions 78, 80 are configured to assist a pair of side surfaces 82, 84 of the tab 32 proximate each respective dome-shaped portion 78, 80 to flex laterally. A closure mechanism 34 is disposed on the first and second walls 20, 22 that is configured to maintain the tab 32 in a plurality of positions. First and second protrusions 36, 38 extend into the cavity 26. The first and second protrusions 36, 38 are configured to contact the blade 12.

Referring now to FIG. 1, the blade disarmer 10 includes the base member 14 and the cover member 24 that is configured to removably attach to the base member 14. The base member 14 and the cover member 24 define the blades-receiving cavity 26 therebetween. The cavity 26 may be accessible on at least the bottom portion 18 of the base member 14 at an insertion opening 44. The cover member 24 is configured to engage with the closure mechanism 34 on the base member 14 for retaining the blade 12 within the cavity 26.

In one embodiment, the base member 14 and the cover member 24 are fabricated from a molded polymer, such as homopolymer or copolymer polypropylene. It will be appreciated, however, that any practicable material may be used. The cover member 24 includes a hinge 28 that separates the body portion 30 from the tab 32. Accordingly, the hinge 28 allows the tab 32 to rotate relative to the body portion 30. The tab 32 is releasably engageable with a portion of the base member 14 through the use of the closure mechanism 34. When closed, the base member 14 and the cover member 24 define the blades-receiving cavity 26 within which blades are contained. It will be appreciated that the blades-receiving cavity 26 is generally configured to receive and secure blades 12 of varying sizes.

Figure 2:
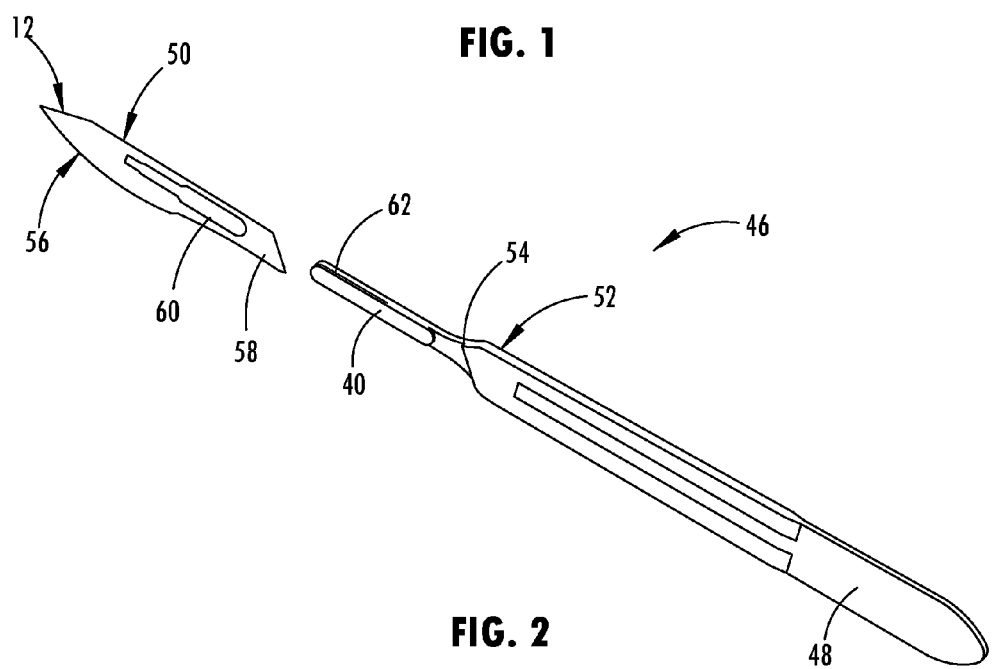
FIG. 2 is a top perspective view of a scalpel with a blade disengaged from a handle.

FIG. 2 generally illustrates a scalpel 46 that includes the removable blade 12. The blade 12 is disposed on a tang 40 that extends from a handle. The handle 48 is provided with a forward body section 52, which gradually narrows in width into the forwardly extending tang 40 at a shoulder portion 54. The blade 12 includes a proximal cutting portion 56 and a distal heel portion 58. In order to mount the blade 12 on the handle 48, an aperture 60 defined by the blade 12 is inserted into grooves 62 on the tang 40. The blade 12 is then slid towards the handle 48 and within the grooves 62. In this way the blade 12 is locked onto the tang 40 and securely held in a desired position.

Referring to FIGS. 3-4, the elongated portion 16, the bottom portion 18, and the pair of external walls 20, 22 extending substantially transversely from the elongated portion 16 of the blade disarmer 10 are illustrated. The base member 14 may further include a plurality of intermediate walls 64a, 64b, 64c, 64d such that a plurality of independent cavities 26a, 26b, 26c, 26d, 26e are defined therebetween. As shown, the base member 14 includes four intermediate walls 64a, 64b, 64c, 64d between the external walls 20, 22 thereby forming five cavities 26a, 26b, 26c, 26d, 26e within the blade disarmer 10. In such an arrangement, the cover member 24 includes five corresponding tabs 32a, 32b, 32c, 32d, 32e disposed between each pair of adjacently disposed walls 20 and 64a, 64b, 64c, 64d, 22. It will be appreciated, however, that the blade disarmer 10 may include any number of cavities. Moreover, any features described herein may be in any orientation without departing from the concepts of the present disclosure.

As illustrated in FIG. 3A, the closure mechanism 34 generally includes an open detent 70 and a closed detent 72. Each tab 32 is configured to rotate about the hinge 28 (FIG. 3) to engage one of the detents 70, 72. Accordingly, the closure mechanism 34 retains the tab 32 in a plurality of pre-defined locations. Thus, the tab 32 and the base member 14 cooperate to entrap blades 12 therebetween for disposal according to safety standards. Moreover, the inwardly extending detents 70, 72 have tapered surfaces thereon to form a saw tooth geometry such that the tabs 32 are easily pressed into lower positions. The base member 14 and the cover member 24 may be made of a stiff, but resiliently flexible material. The flexibility of the walls 20, 64a, 64b, 64c, 64d, 22 permits each tab 32 to be press fit between the opposing pairs of detents 70, 72, whereupon the detents 70, 72 hold the tab 32 in a substantially constant and level position.

With further reference to FIG. 3A, the external and intermediate walls 20 and 64a, 64b, 64c, 64d, 22 each extend above each corresponding tabs 32a, 32b, 32c, 32d, 32e of the cover member 24 when the tabs 32a, 32b, 32c, 32d, 32e cooperate with the open detent 70. Accordingly, a blunt object that is wider than the distance between two adjacently disposed walls 20 and 64a, 64b, 64c, 64d, 22 may not rotate the tab 32a, 32b, 32c, 32d, 32e from engagement with the open detent 70 to engagement with the closed detent 72. Such a configuration may be advantageous during transportation of the blade disarmer 10 where inadvertent contact may be may to portions of the cover member 24.

As shown in FIG. 4, a plurality of partitions 74a, 74b, 74c, 74d isolates a plurality of cavities 26a, 26b, 26c, 26d, 26e from adjacently disposed cavities 26a, 26b, 26c, 26d, 26e. The plurality of partitions 74a, 74b, 74c, 74d extend forwardly and each intermediate wall 64a, 64b, 64c, 64d extends from the plurality of partitions 74a, 74b, 74c, 74d. Each of the plurality of partitions 74a, 74b, 74c, 74d define a base member aperture 76. The base member aperture 76 is configured such that the closure mechanism 34 may be integrally formed with the base member 14 through any process known in the art, including, but not limited to, injection molding.

FIGS. 5-6 generally illustrate a front and a rear view of the blade disarmer 10. As illustrated in FIG. 5, each tab 32a, 32b, 32c, 32d, 32e includes the pair of forwardly extending dome-shaped portions 78, 80 proximate to two opposing side surfaces 82, 84 thereof. The two dome-shaped portions 78, 80 are configured such that the longitudinal side surfaces 82, 84 proximate thereto are flexible in the lateral direction (i.e., transverse to the longitudinal side surfaces 82, 84 of the tab 32) thereby increasing the clearance between the tab 32 and the detents 70, 72 as the tab 32 is rotated through the plurality of positions. Each dome-shaped portion 78, 80, as illustrated, is fully encapsulated such that the blade 12 disposed within the cavity 26 does not protrude therethrough.

Referring to FIG. 5A, the tab 32 further includes a pair of indents 86, 88 having sloped engagement surfaces disposed outwardly of each dome-shaped portions 78, 80. The sloped engagement surfaces of each indent 86, 88 provides additional clearance for each tab 32 to engage with the respective detent 70, 72. As illustrated, the sloped engagement surface of the indents 86, 88 provides for additional clearance for the open and closed detents 70, 72. Likewise, the sloped engagement surface also provides for a uniform engagement surface with a bottom surface of each detent 86, 88. Although the blade disarmer 10 can be pried apart in an emergency, the detents 70, 72 and indents 86, 88 cooperate to lock and to keep the blade disarmer 10 tightly closed.

As shown in FIG. 5A, the open detent 70 and the closed detent 72 are vertically offset from one another along the elongated portion 16 of the base member 14. The offset orientation allowed for each detent 70, 72 to be integrally formed with the base member 14. As illustrated, the open detent 70 has a first width and the closed detent 72 has a second, larger width such that movement from the second position back to the first is more difficult.

As illustrated in FIG. 5, a locking projection 90 is disposed on the bottom portion 18 of the base member 14 proximate a bottom portion 92 of the tab 32 to further prevent inadvertent opening of the cavity 26. The locking projection 90 is disposed proximate to the tab 32 in the second position. Such a configuration makes prying the tab 32 open by the bottom surface 92 of the tab 32 difficult, thereby providing additional safety benefits. The scalpel blade 12 may be transported, and disposed of within a furnace, while it is securely retained within the blade disarmer 10.

Figure 7:
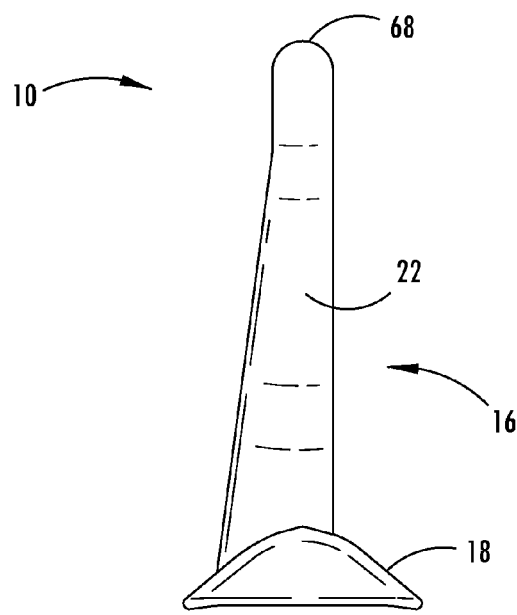
FIG. 7 is a side elevational view of the blade disarmer.
Figure 8:
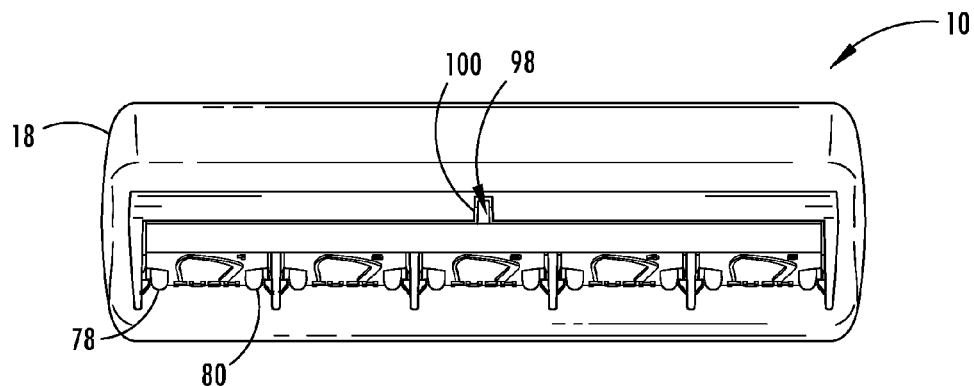
FIG. 8 is a top elevational view of the blade disarmer.
Figure 9:
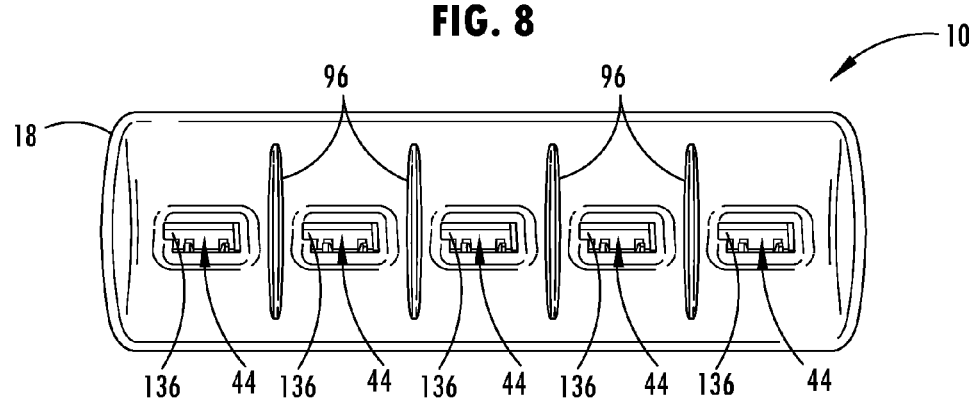
FIG. 9 is a bottom elevational view of the blade disarmer.

Referring to FIGS. 7-9, the blade disarmer 10 includes the semi-circular bottom portion 18 and the vertically extending elongated portion 16. The bottom portion 18 is wider than the elongated portion 16 so that the blade disarmer 10 sturdily rests on a surface proximate the user of the blade disarmer 10. Also, the bottom portion 18 may have a curved surface such that the blade 12 is directed towards the insertion opening 44 as the blade 12 approaches the bottom portion 18. The wide bottom portion 18 also provides a shield between the blade 12 that is inserted through the insertion opening 44 and the user to provide additional safety benefits. Accordingly, the bottom portion 18 may be of a substantially rigid material. It will be appreciated, however, that the bottom portion 18 is configured in any practicable shape such that a cavity 26 for the blades 12 is formed within the blade disarmer 10.

Referring to FIG. 8, the cover member 24 includes a centrally disposed locating feature 98 to assist in attachment of the cover member 24 to the base member 14. As illustrated, the locating feature 98 is configured as a locating flange 100 that is integrally formed with the cover member 24.

As shown in FIG. 9, a plurality of arcuate ribs 96 are disposed on and/or within the bottom portion 18 of the base member 14. The arcuate ribs 96 provide structural support to the base member 14. The arcuate ribs 96 also separate each insertion opening 44 thereby assisting in placement of the blade 12 within a desired insertion opening 44. The arcuate ribs 96 may be integrally formed with the base member 14, or later coupled thereto. Moreover, the arcuate ribs 96 and intermediate wall 64a, 64b, 64c, 64d may have uniform geometry provided therebetween. Such a configuration may assist in preventing sink and/or blemishes on the injection molded base member 14.

Figure 10:
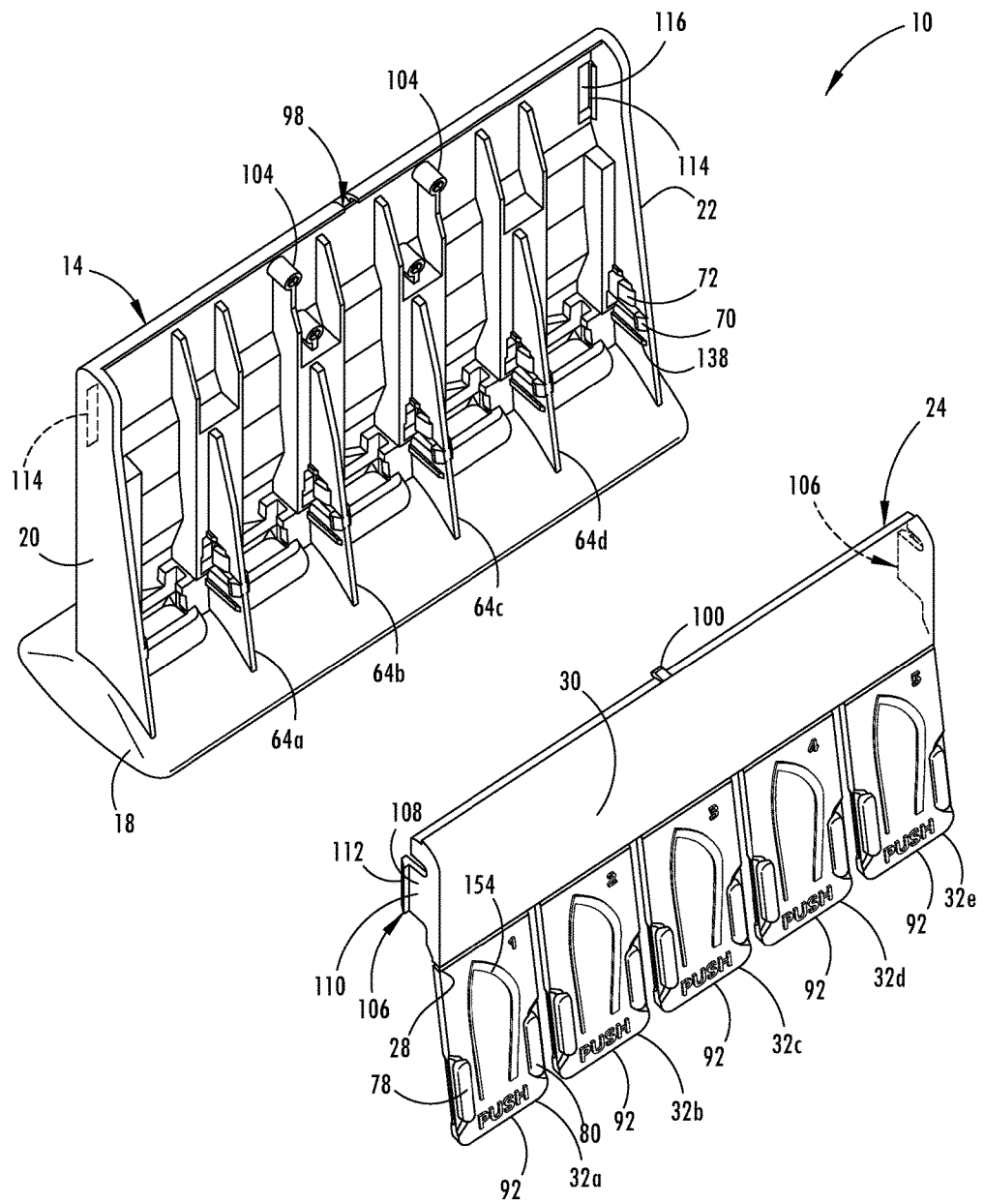
FIG. 10 is an exploded, front perspective view of the blade disarmer.
Figure 11:
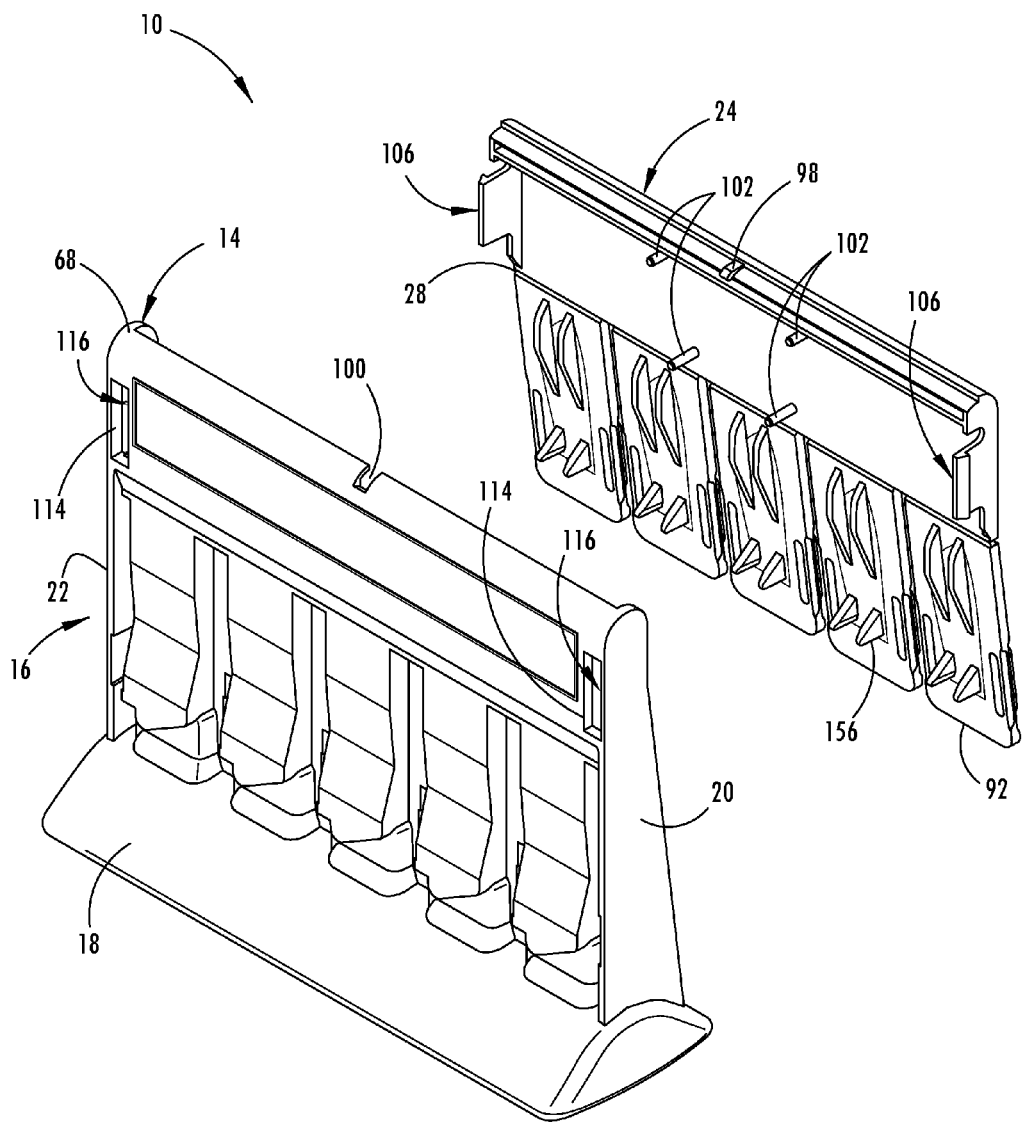
FIG. 11 is an exploded, rear perspective view of the blade disarmer.

Referring to FIGS. 10-11, the cover member 24 and/or the base member 14 includes additional locating features 98 for mating the cover member 24 to the base member 14. According to the illustrated embodiment, the cover member 24 includes a plurality of extensions 102 extending therefrom that is engageable with hollow bosses 104 extending from the base member 14. It should be appreciated, however, that any type of locating feature 98 may be disposed on any portion of the cover member 24, or the base member 14, without departing from the teachings provided herein.

The cover member 24 also includes attachment features 106 coupled to, or integrally formed with, the cover member 24 for removably attaching the cover member 24 to the base member 14. As illustrated, the attachment feature 106 on the cover member 24 is an integrally formed attachment member 108 having a first surface 110 extending in a first direction and a second surface 112 extending in an outwardly, substantially perpendicular direction. The attachment member 108 engages a corresponding base member attachment feature 116. As illustrated, the base member attachment feature 116 is configured as a void 114 through which the attachment member 108 is inserted.

Figure 12:
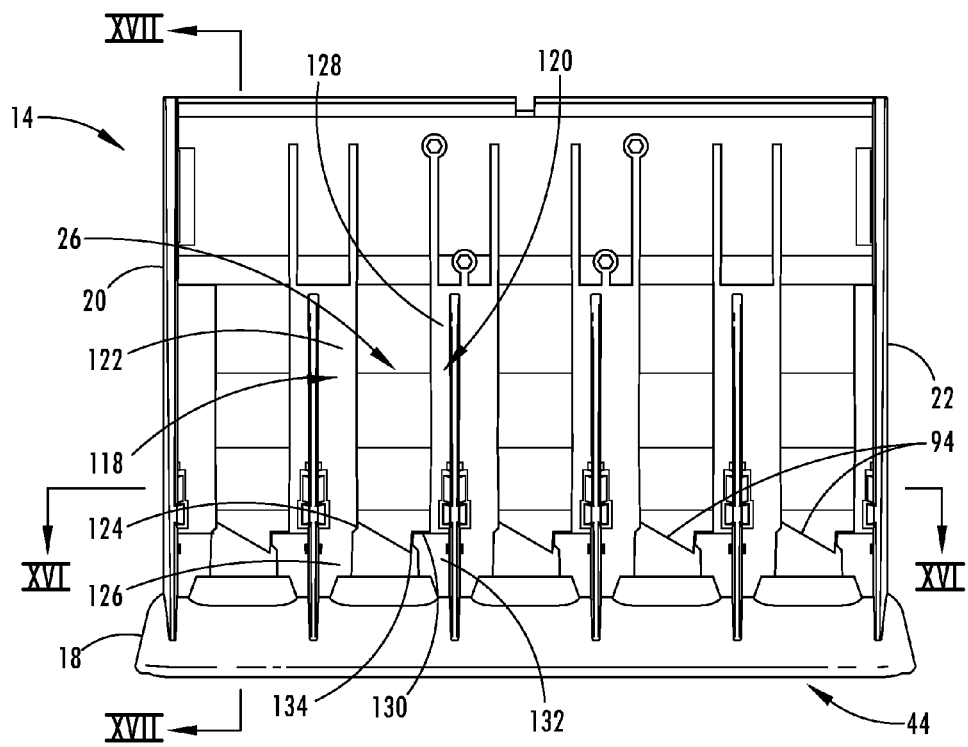
FIG. 12 is a front elevational view of the base member of the blade disarmer.
Figure 13:
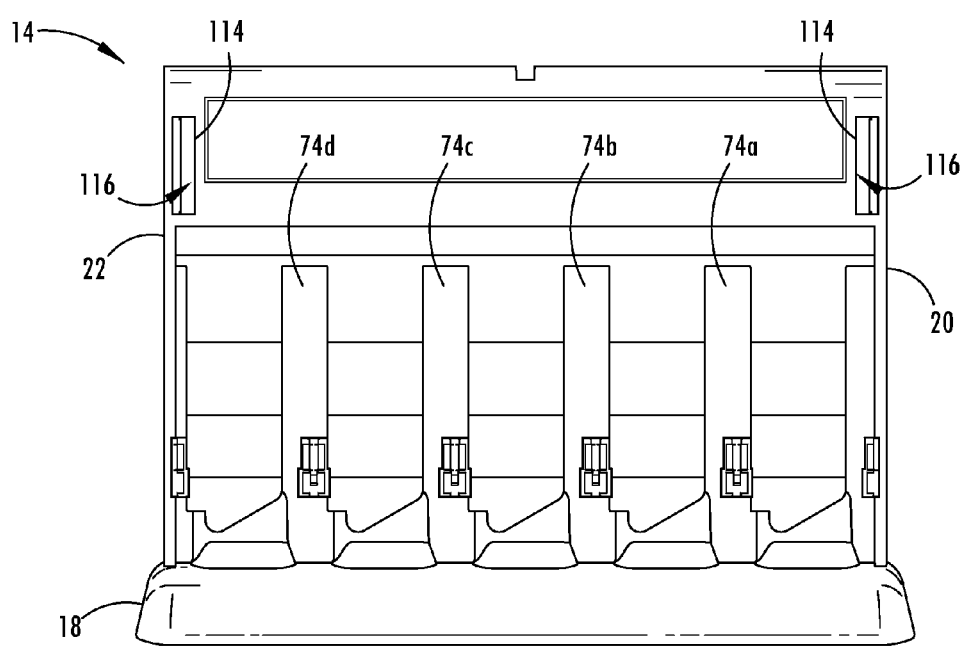
FIG. 13 is a rear elevational view of the base member of the blade disarmer.

Referring to FIGS. 12-13, to assist in placing the handle 48 through the insertion opening 44 and into the cavity 26, the blade disarmer 10 includes a shoulder mating portion 134 within the cavity 26 that is configured to cooperate with a shoulder portion 54 of the scalpel 46. According to one embodiment, the shoulder mating portion 134 is integrally formed with first and second rails 118, 120 disposed within each cavity 26. Each first and/or second rail 118, 120 is defined by a portion of the partition 74a, 74b, 74c, 74d that defines each cavity 26, as described above. The first rail 118 extends inwardly from the first wall 20 defining a first width. The second rail 120 is disposed adjacently to the opposing, second wall 22 of the cavity 26 and extends inwardly therefrom to define a second width.

As illustrated in FIG. 12, the first rail 118 includes a first vertical portion 122 that is substantially parallel with the first wall 20. The first vertical 122 portion terminates at a transition portion 124. The transition portion 124 is configured to reduce the width of a second vertical portion 126 at one end of the transition portion 124 relative to the adjacently located first wall 20. The first rail 118 then maintains the narrower width of the second vertical portion 126 for the remaining length of the first rail 118 and terminates at the bottom portion 18 of the base member 14.

Still referring to FIG. 12, the second rail 120 includes a first portion 128 having a first width that terminates at a substantially perpendicularly extending transition portion 130 that increases the width of the second rail 120 into the cavity 26. The second rail 120 maintains a second width through a second portion 132 until the second rail 120 terminates at the bottom portion 18 of the base member 14. The second portion 132 of the second rail 120 includes the shoulder mating projection 134 extending inwardly into the cavity 26. In some embodiments, the transition portion 130 and the mating projection 134 is configured to be geometrically similar to the shoulder portion 54 of the scalpel handle 48 such that the scalpel 46 is inhibited from further insertion into the cavity 26. Thus, the shoulder mating portion 134 is generally configured to stop the scalpel handle 48 from further insertion into the cavity 26 and/or place the scalpel handle 48 and the blade 12 thereon in the proper orientation.

Figure 14:
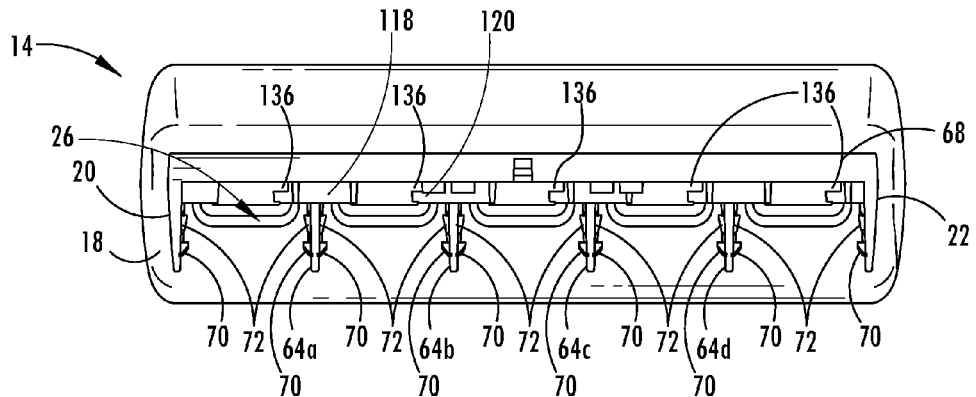
FIG. 14 is a top elevational view of the base member of the blade disarmer.
Figure 15:
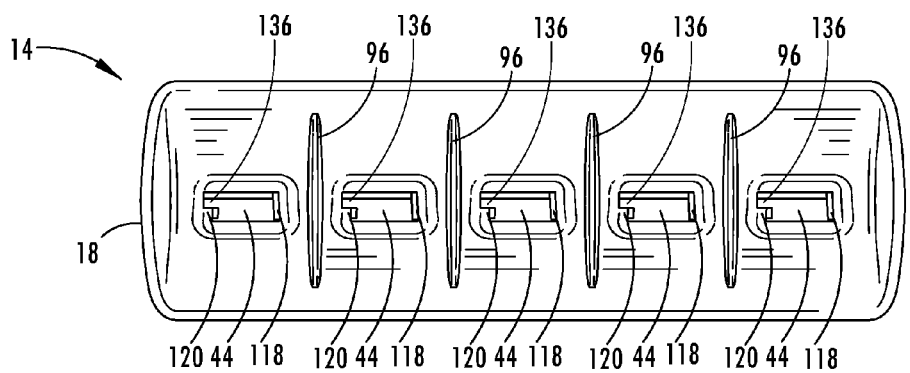
FIG. 15 is a bottom elevational view of the base member of the blade disarmer.
Figure 16:
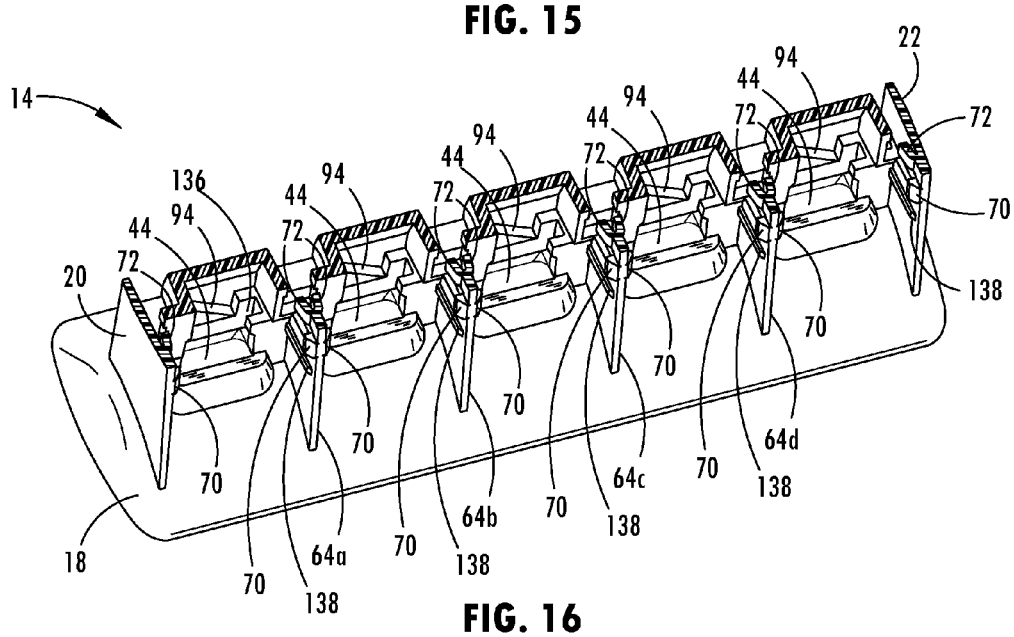
FIG. 16 is a top elevational cross-sectional view of the base member of the blade disarmer taken along XVI-XVI of FIG. 12.

Referring to FIGS. 14-16, the illustrated closure mechanism 34 is configured as open and closed detents 70, 72 extending inwardly into the cavity 26 from the side walls 20, 22 and intermediate wall 64a, 64b, 64c, 64d. More specifically, each wall 20, 64a, 64b, 64c, 64d, 22 includes the first, open detent 70 disposed at a first height above the first rail 118 and the second, closed detent 72 is disposed at a second height above the first rail 118. Corresponding detents 70, 72 at similar heights are disposed above the opposing second rail 120. As illustrated, the second height is less than the first height. It will be appreciated that the blade disarmer 10 may include any number of detents and the included detents 70, 72 may be disposed on any number of walls, forming each respective cavity 26. Further, it will also be appreciated that the closure mechanism 34 may be configured as any other structure such that the tab 32 may be movable between a plurality of positions without departing from the concepts of the present disclosure.

As illustrated in FIG. 14, the open detent 70 retains the tab 32 in a first position wherein the tab 32 is retained from upward rotation by the first, upper detent 70 on each wall 20, 64a, 64b, 64c, 64d, 22, thereby defining a first volume of the cavity 26 between the base member 14 and the tab 32. The closed detent 72 retains the tab 32 in a second position. When the tab 32 is in the second position, a second, smaller volume of the cavity 26 is formed between the tab 32 and the base member 14. Any number of detents 70, 72 may be disposed on the walls 20, 64a, 64b, 64c, 64d, 22, for creating the cavity 26 with a plurality of volumes. It should be appreciated that each cavity 26 may also have a unique volume, such that a plurality of blades 12 may be stored within a plurality of variously sized cavities 26. The unique cavities 26 may be incorporated into a single blade disarmer 10 having a plurality of cavities 26 therein. Alternatively, each unique cavity 26 may be an independent blade disarmer 10 configured to have a single cavity 26, as described above.

As shown in FIG. 14, the open detent 70 extends further into the cavity 26 than the closed detent 72. Thus, it is easier for a user of the blade disarmer 10 to rotate the tab 32 to the second position from the first position versus movement of the tab 32 to a position above the open detent 70.

As shown in FIGS. 15-16, the first or second rail 118, 120 includes a slot 136 below the mating projection 134 disposed on either rail 118, 120 such that the blade 12 that is wider that the distance between the first and second rails 118, 120 is slid into the cavity 26 through the slot 136.

As illustrated in FIG. 16, the exterior and/or intermediate walls 20, 64a, 64b, 64c, 64d, 22 may include any number of ribs 138 thereon to provide structural support for the walls 20, 64a, 64b, 64c, 64d, 22, and/or to provide additional positional functions for components of the blade disarmer 10. For example, the ribs 138 may assist in centrally locating each tab 32 through the plurality of positions.

Still referring to FIG. 16, each cavity 26 includes a blade mating portion 94 proximate the bottom of each respective cavity. The blade mating portion 94 may have a geometry that is substantially similar to the distal heel portion 58 of the scalpel blade 12. The blade mating portion 94 is configured to contact the distal heel portion 58 of the blade 12 disposed within the cavity 26. Accordingly, the blade mating portion 94 prevents the removed blade 12 from exiting the cavity 26 through the insertion opening 44.

Figure 17:
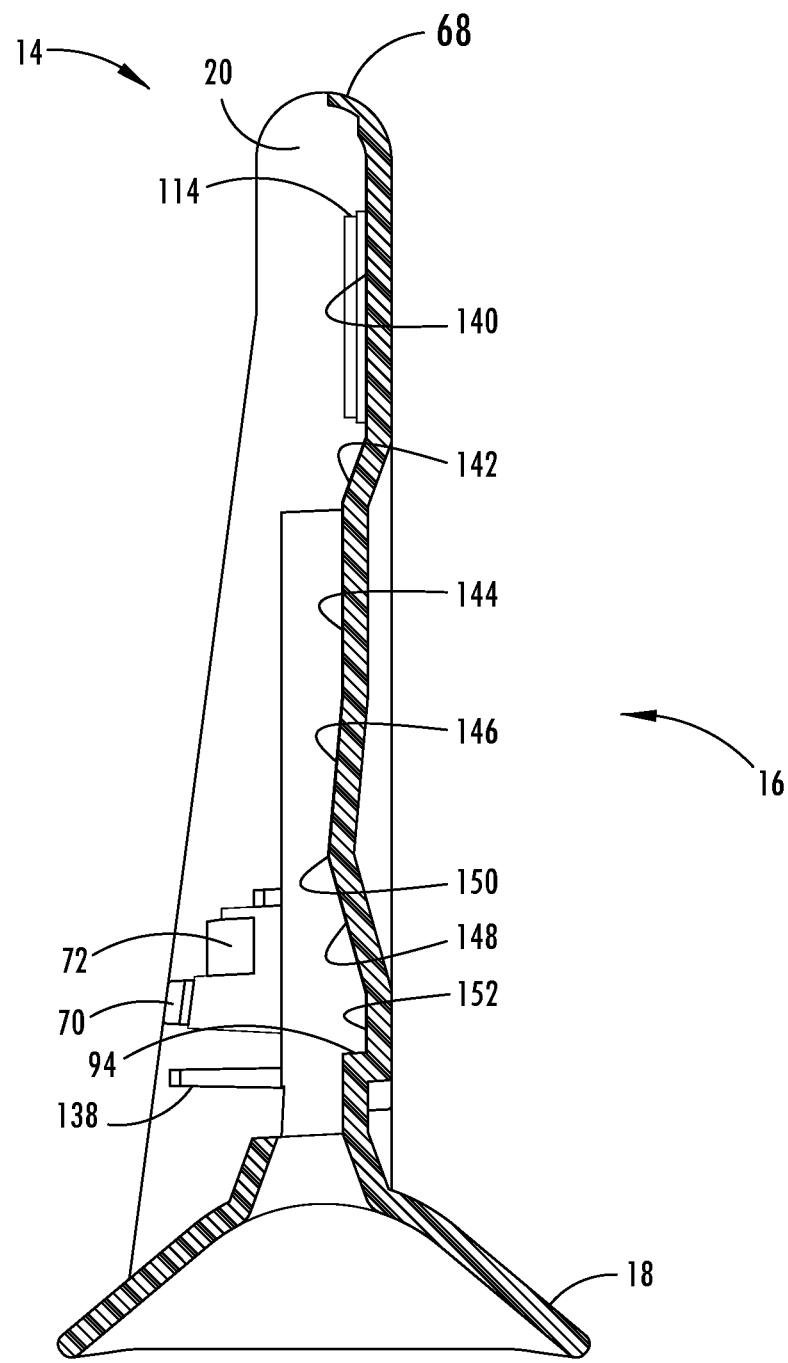
FIG. 17 is a side elevational cross-sectional view of the base member taken along XVII-XVII of FIG. 12.

As illustrated in FIG. 17, the elongated portion 16 of the base member 14 includes a plurality of surfaces extending from the top portion 68 of the base member 14 and terminating at the bottom portion 18. A first substantially planar surface 140 extends from the top portion 68 to a first transition surface 142. The first transition surface 142 is disposed at a first obtuse angle to the first surface 140 and terminates at a second surface 144 that is forwardly of the first surface 140. A second transition surface 146 extends from the second surface 144 at a second obtuse angle. A third rearwardly orientated surface 148 is disposed at the opposing end of the second transition surface 146 forming an apex 150 between the second transition surface 146 and the third surface 148. A fourth surface 152 is disposed between the third surface 148 and bottom portion 18 of the base member 14. The fourth surface 152 is incorporated into the shoulder mating portion 134 that is configured to substantially correlate to the geometry of the distal heel portion 58 of the blade 12. It should be appreciated that the base member 14 may include any number of portions and that the apex 150 may be formed in any manner known in the art. It should further be appreciated that the apex 150 may be disposed at any location along the base member 14.

Figure 18:
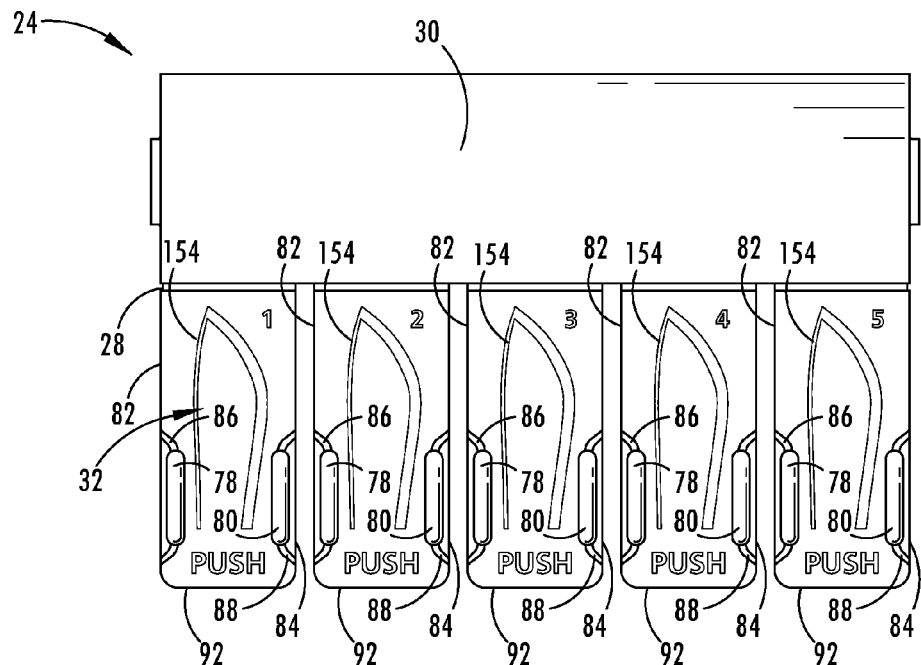
FIG. 18 is a front elevational view of the cover member.
Figure 19:
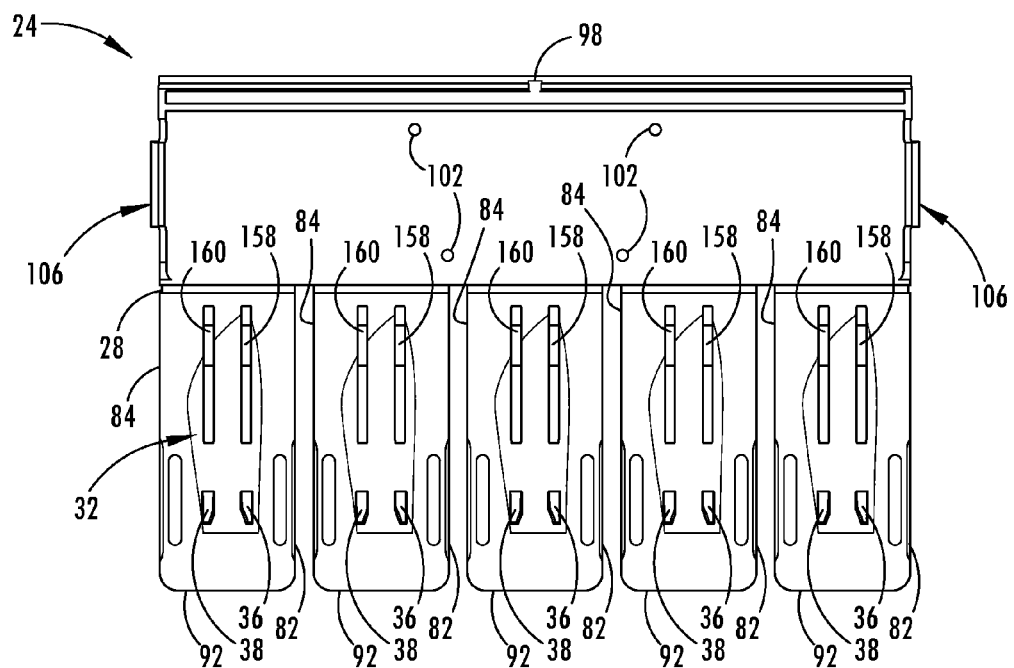
FIG. 19 is a rear elevational view of the cover member.
Figure 20:
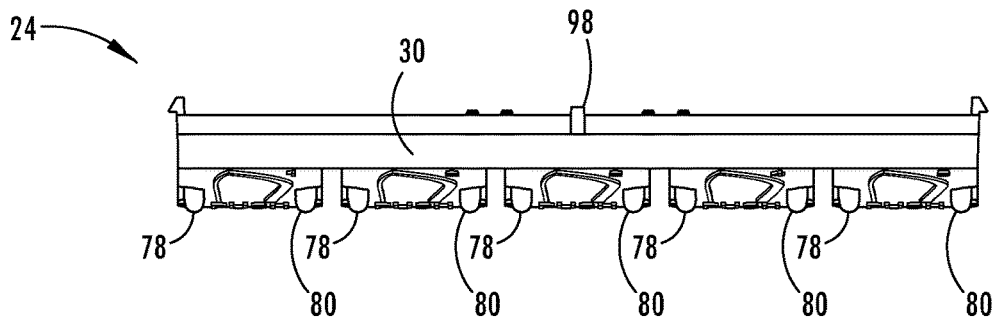
FIG. 20 is a top elevational view of the cover member.

Referring to FIG. 18, the cover member 24 includes the body portion 30 and a plurality of tabs 32. A hinge 28 separates each tab 32 from the body portion 30. The hinge 28 is a flexible hinge that is integrally formed within the cover member 24 to separate the body portion 30 from the tabs 32. The hinge 28 has a recess or cut about which the living hinge 28 can rotate. In some embodiments, the hinge 28 is a living flexible hinge (e.g., flexure bearing) made from the same material as the other portions of the cover member 24. In alternate embodiments, an additional component may be added to the assembly to form the hinge 28. The additional component may be any type of hinge 28 known in the art.

As shown in FIG. 18, indicia 154 is disposed on the cover member 24 and/or the tabs 32 for assisting a user of the blade disarmer 10. As illustrated, each tab 32 includes an outline of the blade 12 centrally located thereon. The outline of the blade 12 represents the correct orientation for insertion of the blade 12 into the cavity 26. The indicia 154 also incrementally numbers each tab 32 for assisting in counting the used blades 12 stored within any of the cavities 26a, 26b, 26c, 26d, 26e (FIG. 5). The indicia 154 may be disposed on any portion of the blade disarmer 10 during forming of any component, or later disposed thereon.

As shown in FIGS. 19-22, the tab 32 is rotatable relative to the body portion 30 about the hinge 28. Each tab 32 includes the pair of protrusions 36, 38 that are transversely spaced apart by a separation sufficient to accommodate the width of the tang 40 on the scalpel handle 48. Each tab 32 includes a pair of elongated ribs 158, 160 disposed between the protrusions 36, 38 and the hinge 28. The elongated ribs 158, 160 are configured to cooperate with the back surface of the base member 14 such that the proximal cutting portion 56 of the blade 12 disposed therebetween is held in a desired position through contact between the elongated ribs 158, 160, and the base member 14. According to one embodiment, the elongated ribs 158, 160 and the base member 14 maintain the proximal cutting portion 56 of the blade 12 in a substantially planar, vertical orientation. Through the use of the pair of elongated ribs 158, 160 to control the deflection of the proximal cutting portion 56 of the blade 12, a more repeatable removal and storage process is created. The removed scalpel blade 12 encapsulated within the cavity 26 of the blade disarmer 10 is visible through the tab 32, which is made of a transparent or translucent material.

Figure 21:
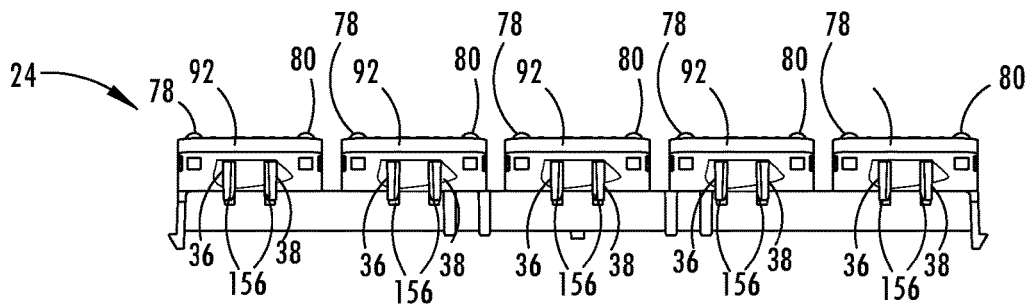
FIG. 21 is a bottom elevational view of the cover member.

As illustrated in FIG. 21, the first and second protrusions 36, 38 have an angled bottom surface 156 that provides additional clearance between the bottom surface 156 and the tang 40 of the scalpel 46 as the first and second protrusions 36, 38 contact the distal heel portion 58 of the blade 12. Additionally, the protrusions 36, 38 have the curved bottom surface 156 such that a constant amount of contact is maintained as the tab 32 is rotated through the plurality of positions.

Figure 22:
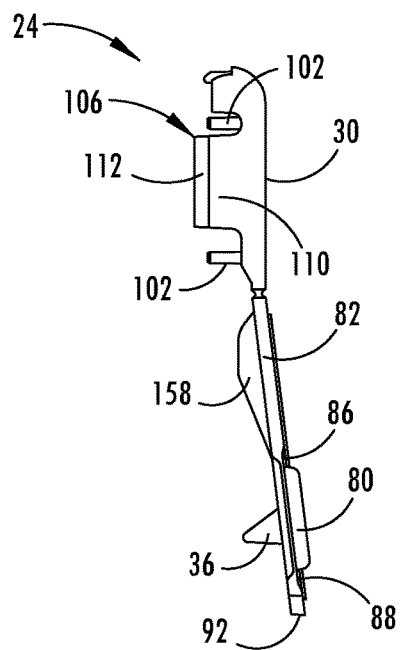
FIG. 22 is a side elevational view of the cover member.
Figure 22A:
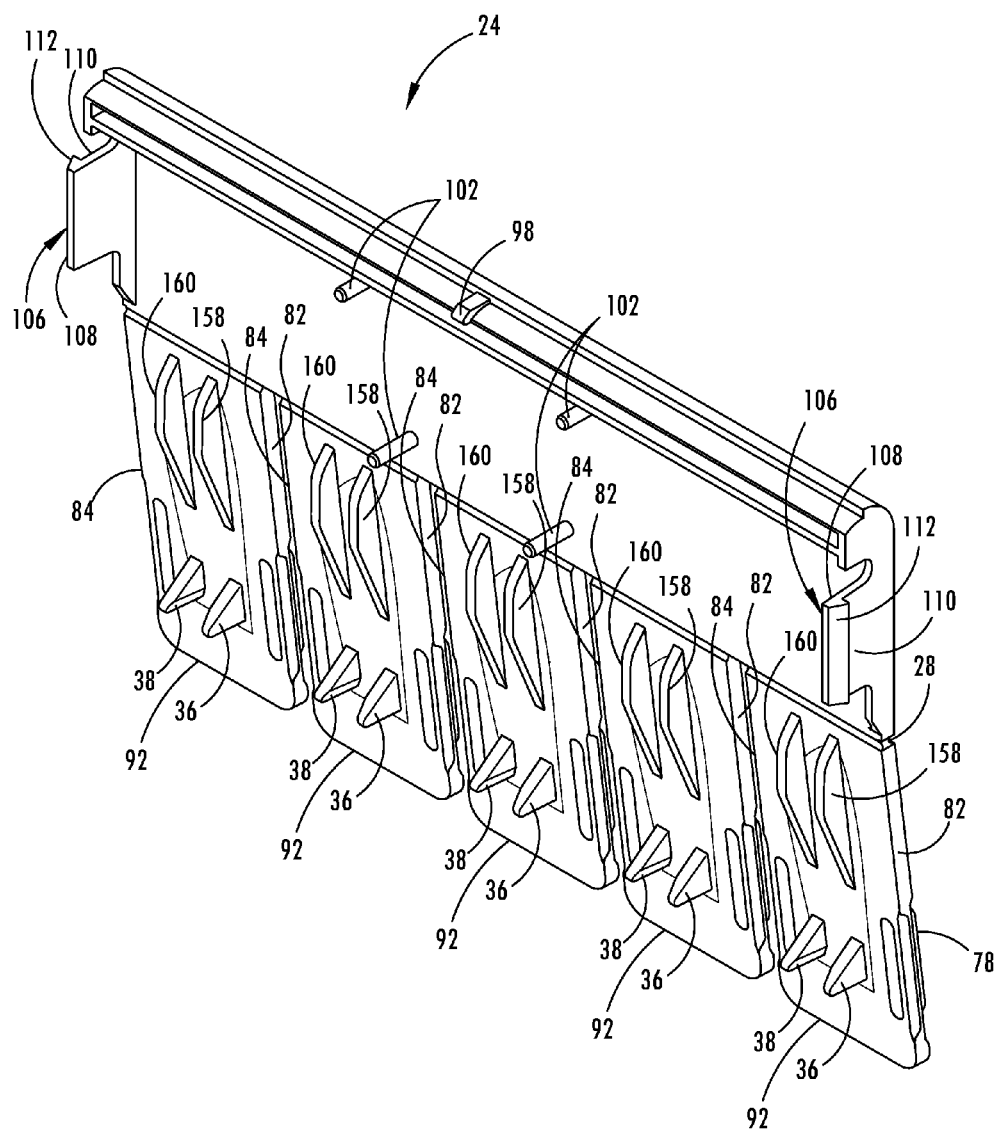
FIG. 22A is a rear perspective view of the cover member.

As shown in FIG. 22A, the elongated ribs 158, 160 maintain a parallel orientation to one another. Moreover, the elongated ribs 158, 160 extend into the cavity 26 at a length that is less than that of the protrusions 36, 38. Each elongated rib 158, 160 also have a linear top surface such that the top surface remains in contact with a desired portion of the proximal cutting portion 56 of the blade 12. The elongated ribs 158, 160 are configured to hold a portion of the blade 12 between the tab 32 and the elongated portion 16 of the base member 14.

With reference now to FIGS. 23-27D, the procedure whereby a blade 12 is safely removed from the scalpel handle will now be discussed. The blade disarmer 10 is configured to remove the blade 12 from the scalpel handle 48 within the cavity 26. In order to remove the blade 12 from the handle 48, the blade 12 is forced out of plane and away from the handle 48 until the blade 12 disengages from the tang 40. The blade 12 and the handle 48 are then slid relative to one another until the tang 40 is removed from the aperture 60 in the blade 12. Accordingly, as described above, the cover member 24 includes the pair of protrusions 36, 38 and the pair of elongated ribs 158, 160 that extend transversely from the cover member 24 into the cavity 26. The protrusions 36, 38 is disposed on opposing sides of the tang 40 and configured to press against the distal heel portion 58 of the blade 12. The elongated ribs 158, 160 are configured to maintain planar orientation of the proximal cutting portion 56 of the blade 12. As the blade 12 is bent from its planar orientation, the tang 40 is removed from the aperture 60 in the blade 12 and the handle 48 is removed from the blade disarmer 10.

Figure 23:
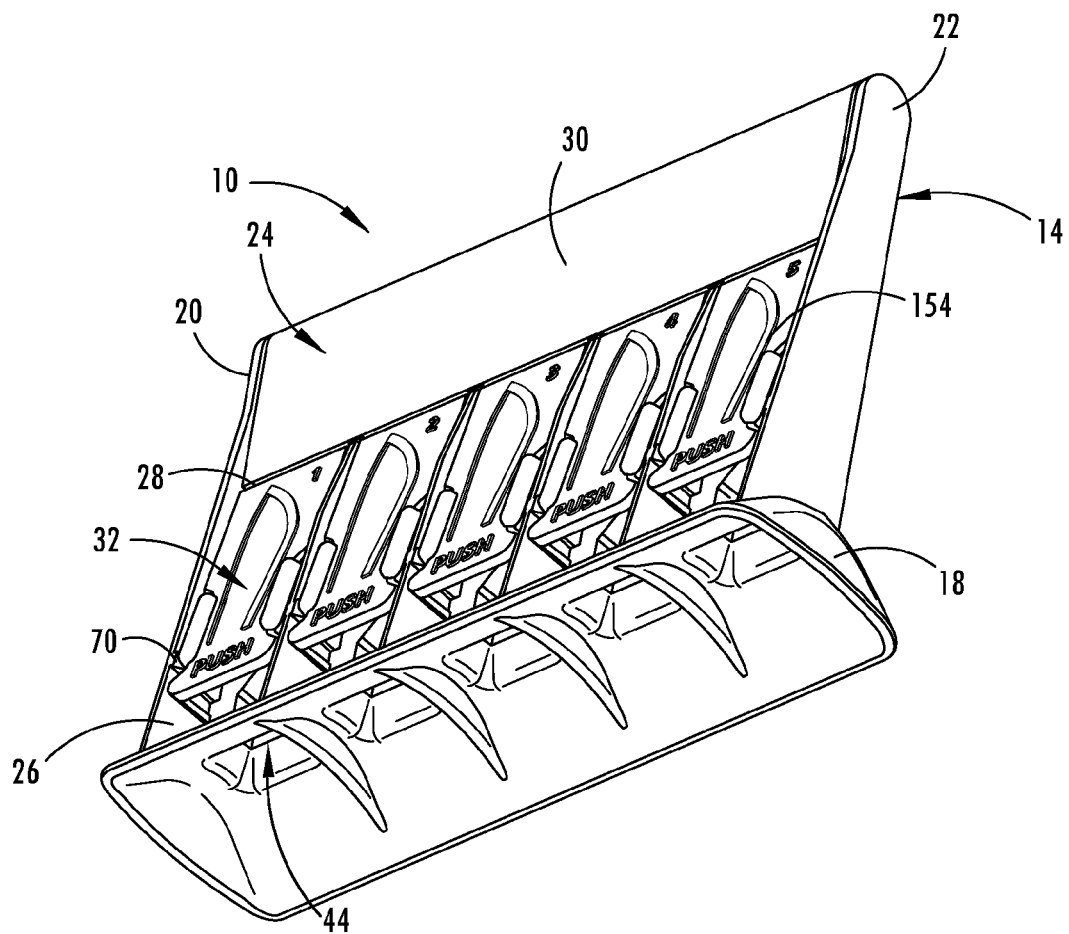
FIG. 23 is a front bottom perspective view of the cover member attached to the base member.

As shown in FIG. 23, the blade disarmer 10 initially has a tab 32 disposed below the open detent 70. Additionally, the insertion opening 44 is configured to accept a blade 12 and portion of the scalpel handle 48 therethrough in the orientation identified by the indicia 154.

Figure 24:
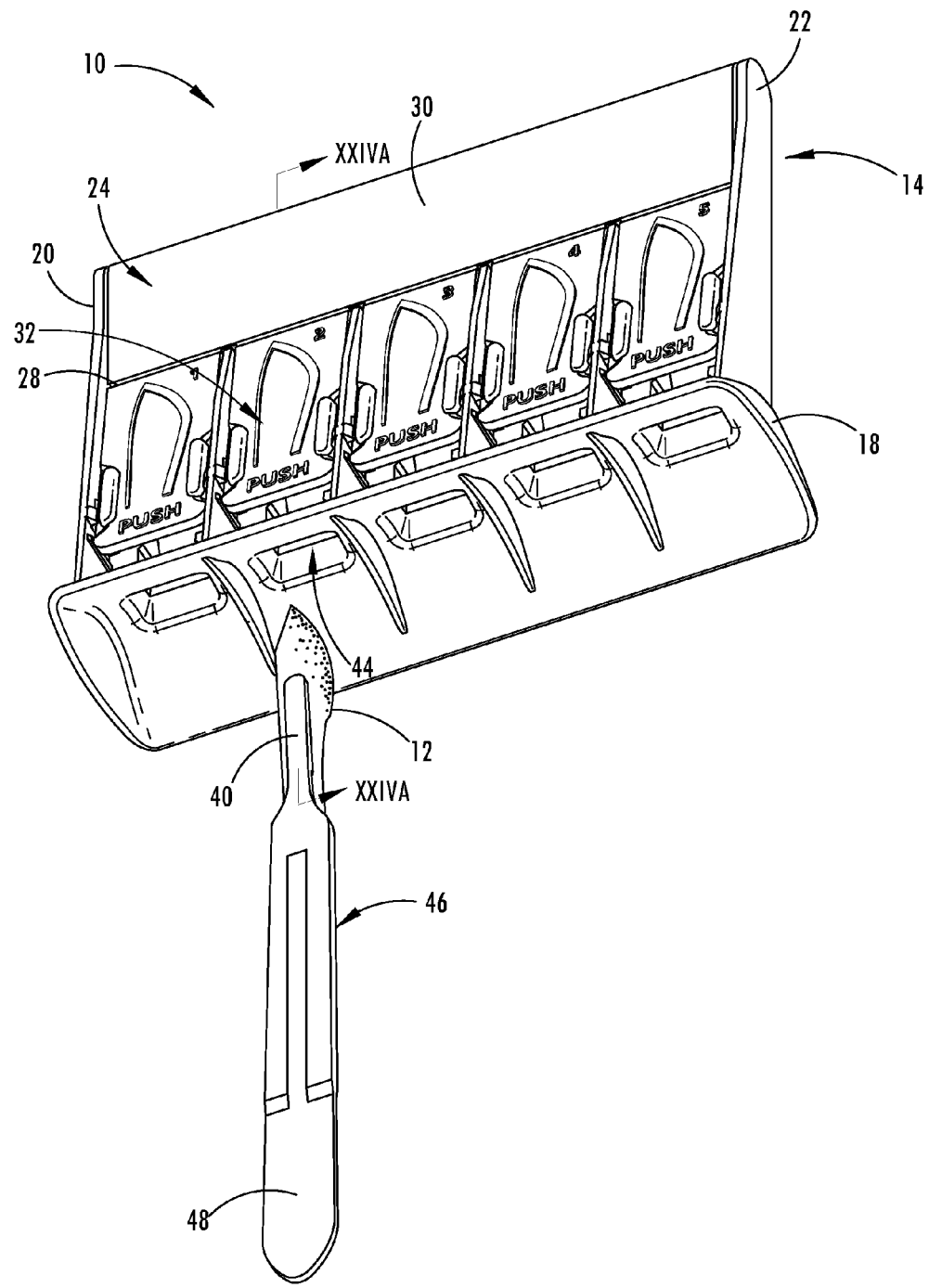
FIG. 24 is a bottom front perspective view of the blade disarmer and the scalpel prior to placement of the blade through an insertion opening.
Figure 24A:
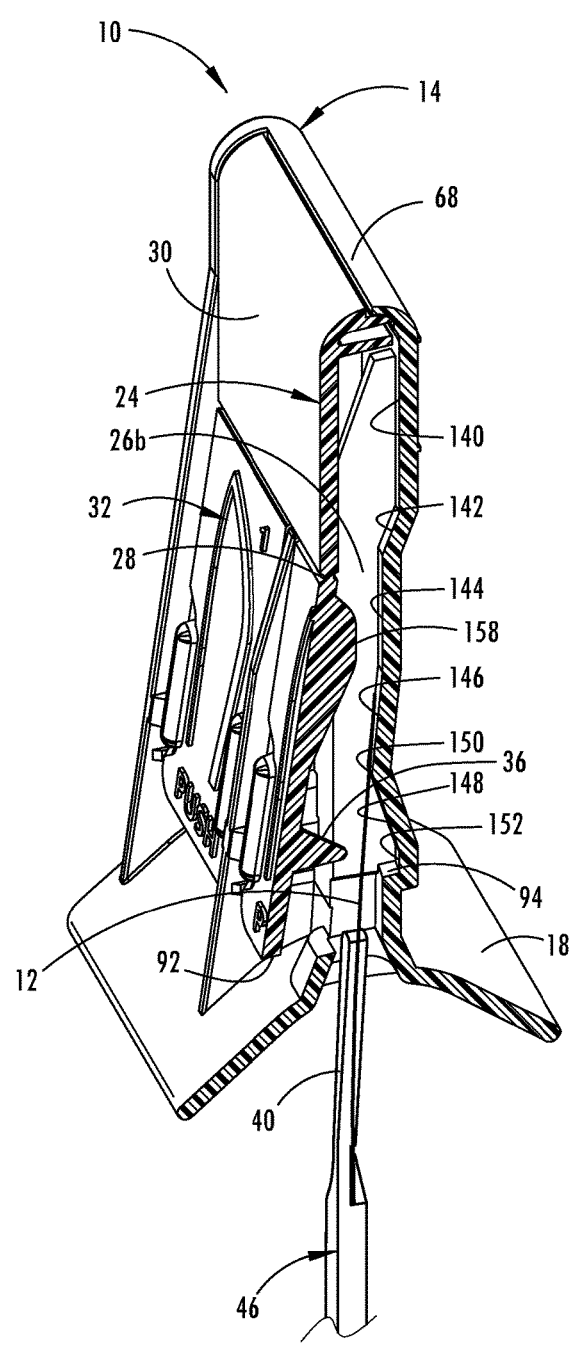
FIG. 24A is a front perspective cross-sectional view taken along XXIVA-XXIVA of FIG. 24 illustrating the blade disarmer having a blade partially inserted into a cavity formed between the base member and the cover member.
Figure 24B:
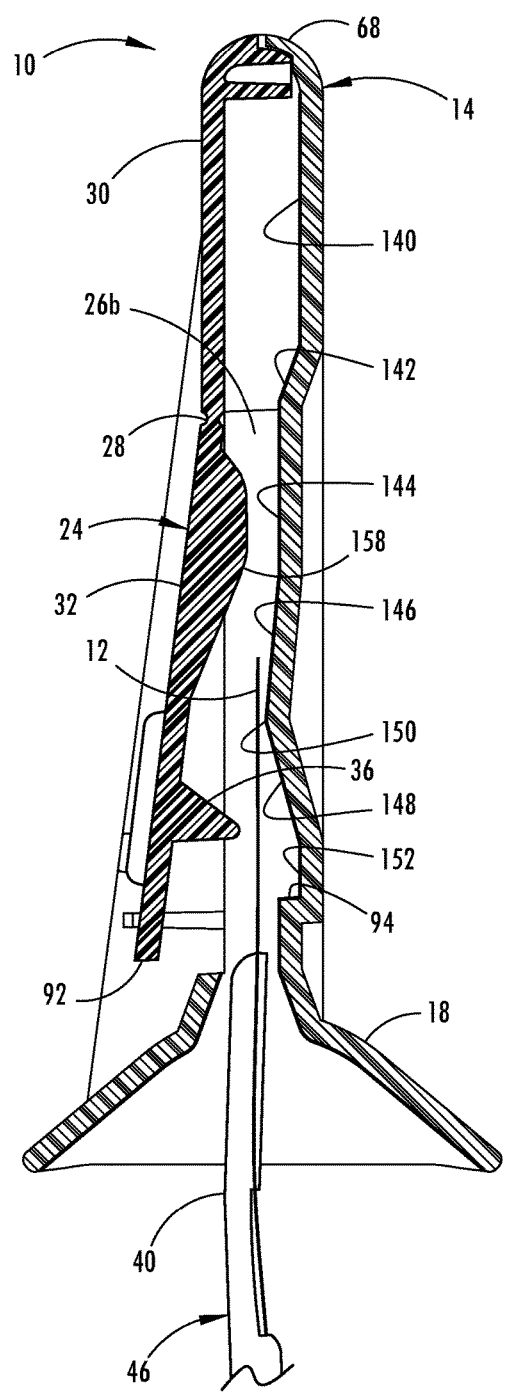
FIG. 24B is a side elevational cross-sectional view taken along the line XXIVA-XXIVA of FIG. 24 illustrating a blade partially inserted into the cavity.

As shown in FIGS. 24-24C, the blade 12 is placed within a desired cavity 26 through the insertion opening 44 disposed on the bottom portion 18 of the base member 14. The blade 12 is orientated in manner consistent with the indicia 154 disposed on the tab 32. As illustrated the blade 12 is oriented such that the tang 40 is disposed forwardly of the blade 12.

The blade 12 may be wider than the distance between the first and second rail 118, 120 and/or the shoulder portion 54 of the cavity 26. Accordingly, a slot 136 is disposed below the mating projection 134 such that a blade 12 that is wider may still be inserted into the cavity 26. The blade 12, in the described position, is disposed between the first and second rails 118, 120. Moreover, the tab 32 is in the first position and the protrusions 36, 38 and the elongated ribs 158, 160 are disposed forwardly of the blade 12 such that the blade is not inhibited from inward movement by either the protrusions 36, 38 or the elongated ribs 158, 160.

Figure 25:
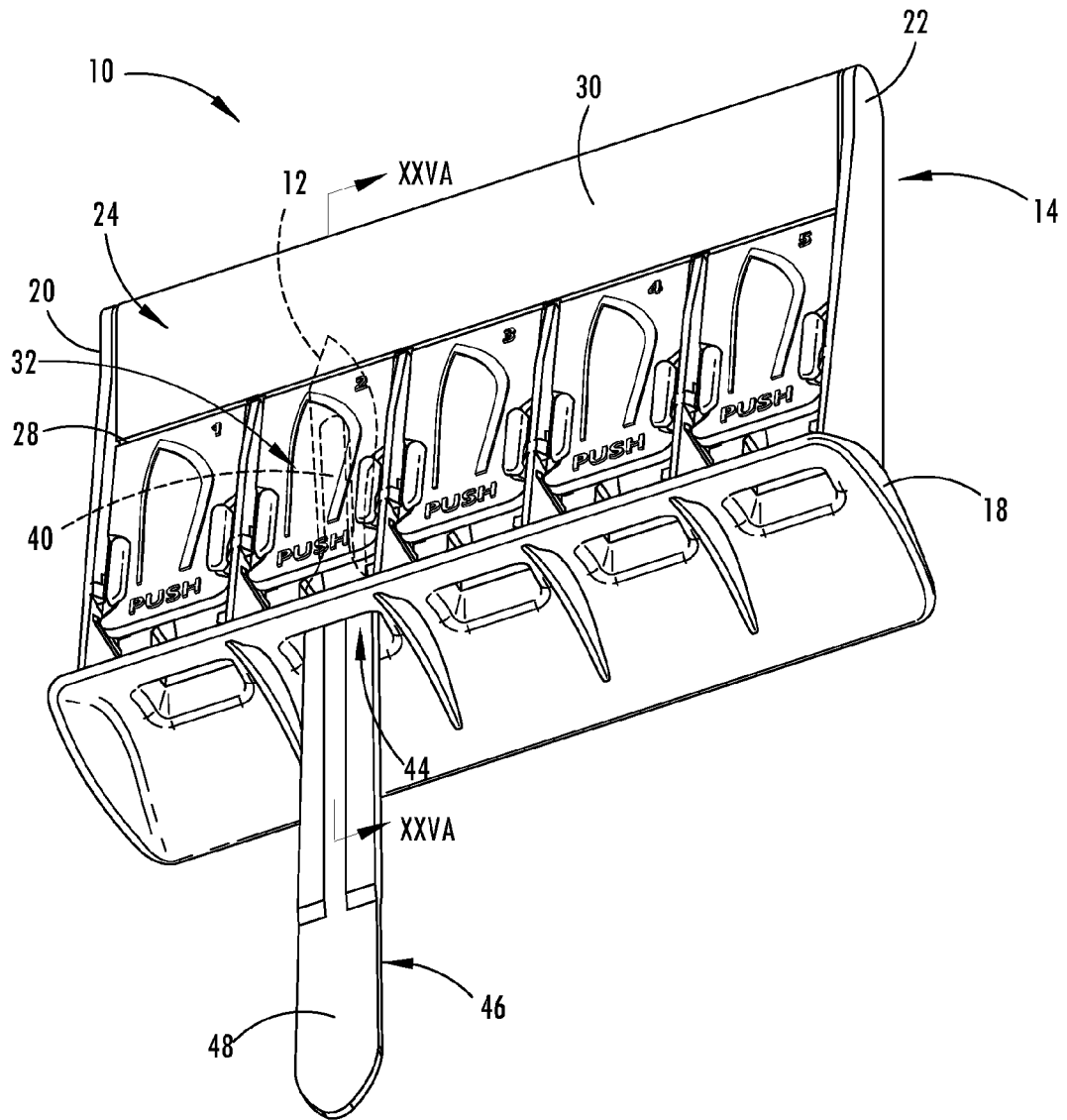
FIG. 25 is a bottom perspective elevational view of the blade fully inserted into the cavity.

As shown in FIGS. 25-25D, the blade 12 is inserted into the cavity 26 until the shoulder portion 54 of the scalpel 46 contacts the shoulder mating portion 134 within the cavity 26. As such a point, the blade 12 is fully disposed within the cavity 26. The protrusions 36, 38 and the elongated ribs 158, 160 are disposed in a first location so as not to interfere with insertion of the blade 12 into the cavity 26. Also, the blade 12 is inserted and oriented in the manner that matches the indicia 154 disposed on the tab 32 thereby ensuring proper orientation of the blade 12 and the tang 40 within the cavity 26.

As illustrated in 26-26D, once the scalpel blade 12 is inserted into the cavity 26, as shown in FIG. 25C, the hinged tab 32 is depressed towards the base member 14, such as by squeezing force between the thumb and fingers, thereby placing the tab 32 in a second position. It will be appreciated that pressure may be applied to the tab 32 through any means, and is not limited to the squeezing force between the thumb and fingers. For example, pressure may be applied to the tab 32 while the blade disarmer 10 is adhered to a table thereby providing sufficient pressure to depress the tab 32. By act of this hinged movement of the tab 32 relative each of to the body portion 30, the scalpel blade 12 is bent out of plane in its distal heel portion 58 about the apex 150. As discussed above, the elongated ribs 158, 160 hold the proximal cutting portion 56 of the blade 12 in a planar orientation such that the blade 12 can then be removed from the tang 40 of the scalpel 46.

Figure 26:
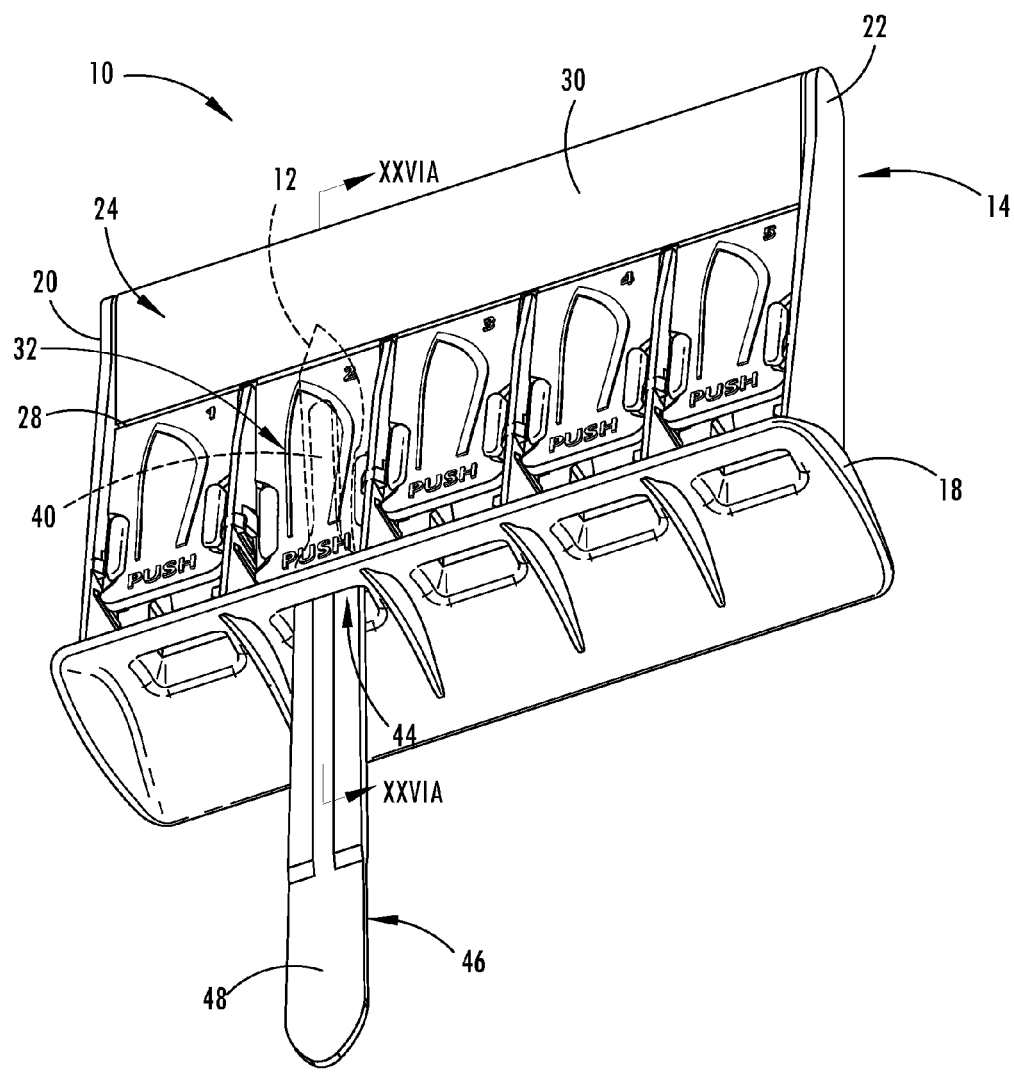
FIG. 26 is a bottom perspective elevational view of the blade fully inserted into the cavity and a tab rotated from a first position to a second position.
Figure 26A:
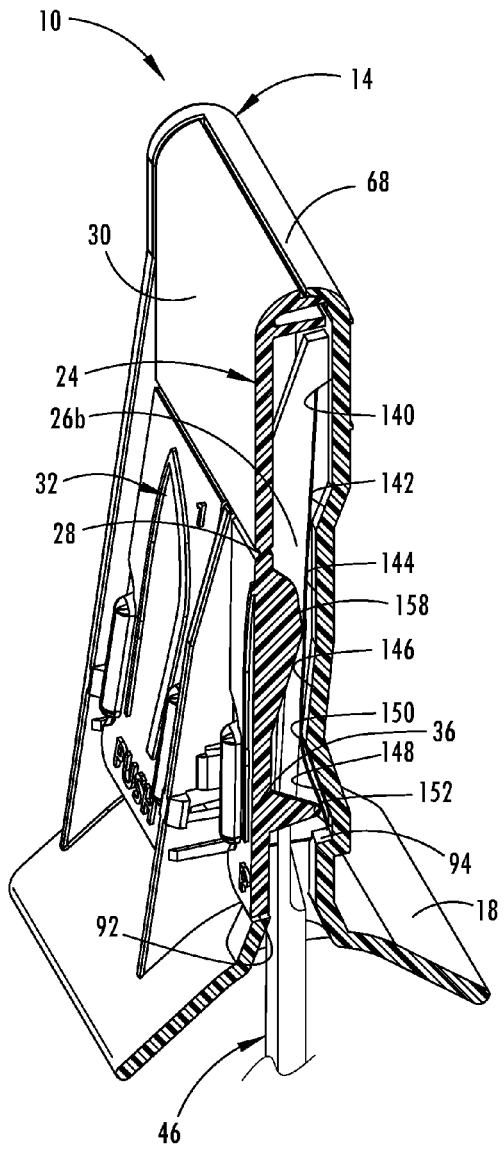
FIG. 26A is a front perspective cross-sectional view taken along XXVIA-XXVIA of FIG. 26 illustrating the blade fully inserted into the cavity and the tab rotated from a first position to a second position.
Figure 26B:
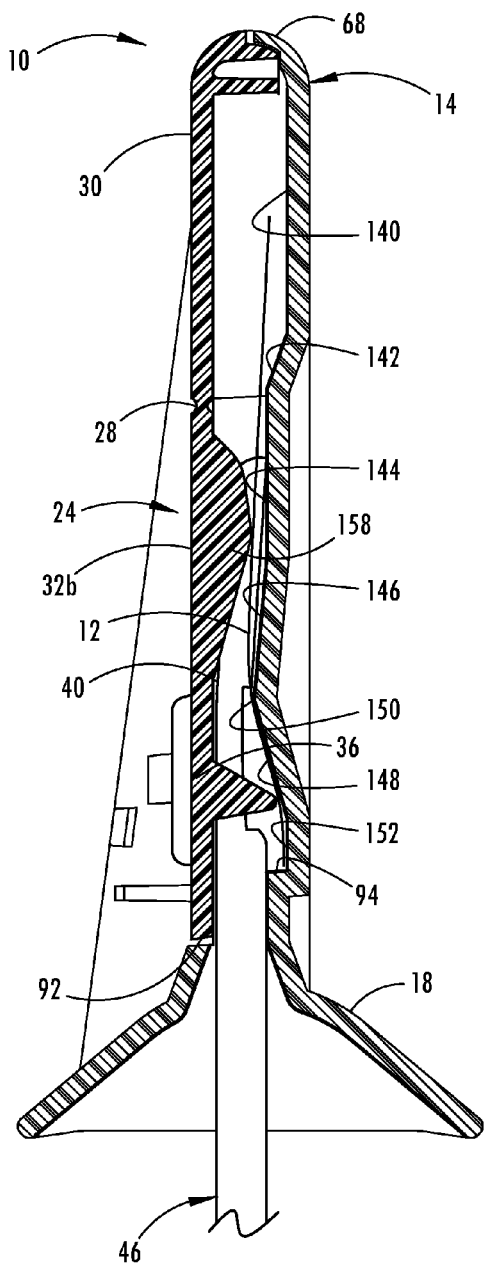
FIG. 26B is a side elevational cross-sectional view taken along the line XXVIA-XXVIA of FIG. 26.
Figure 27:
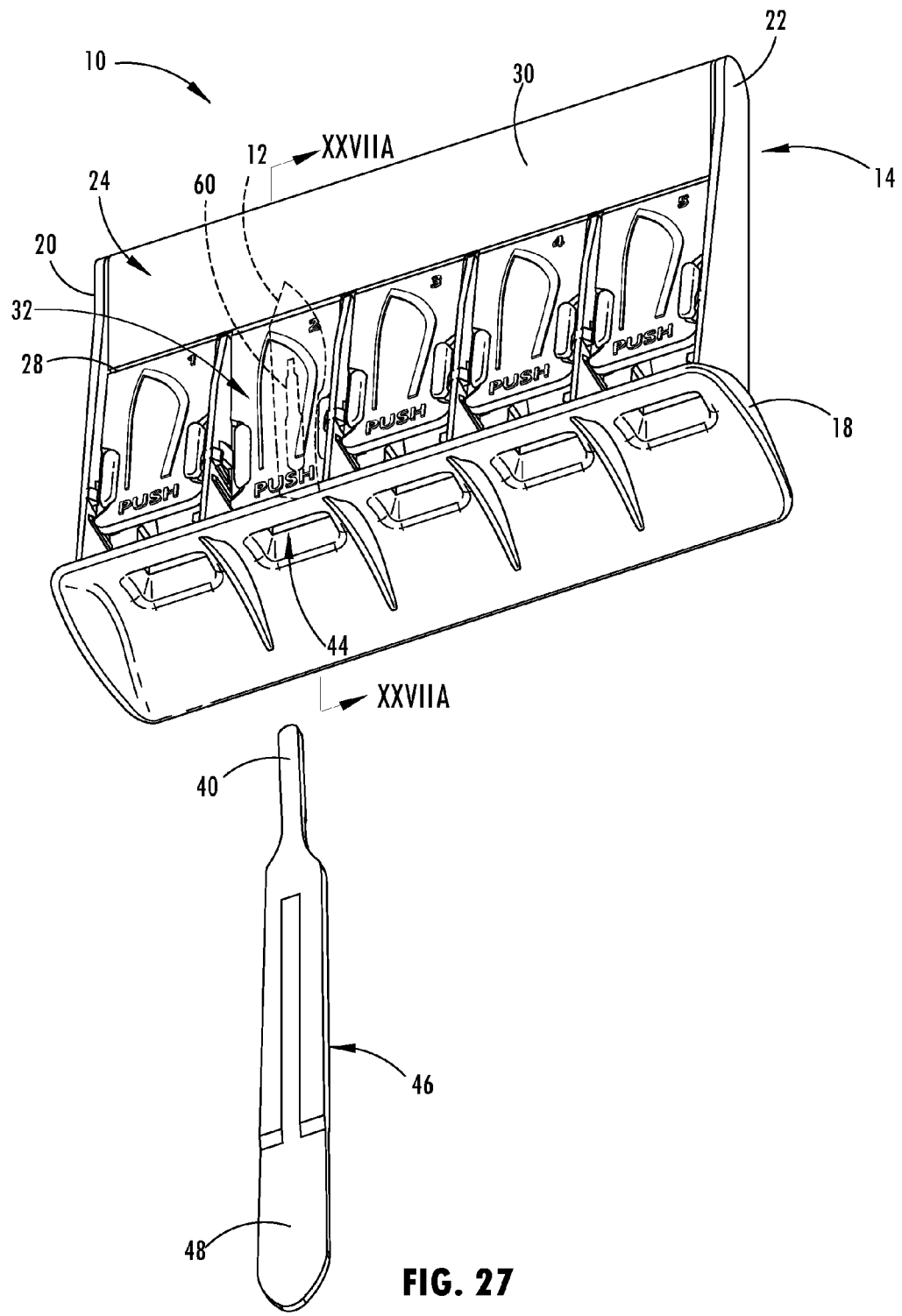
FIG. 27 is a bottom perspective elevational view of a scalpel handle removed from the blade disarmer and the blade disposed with the cavity.
Figure 27C:
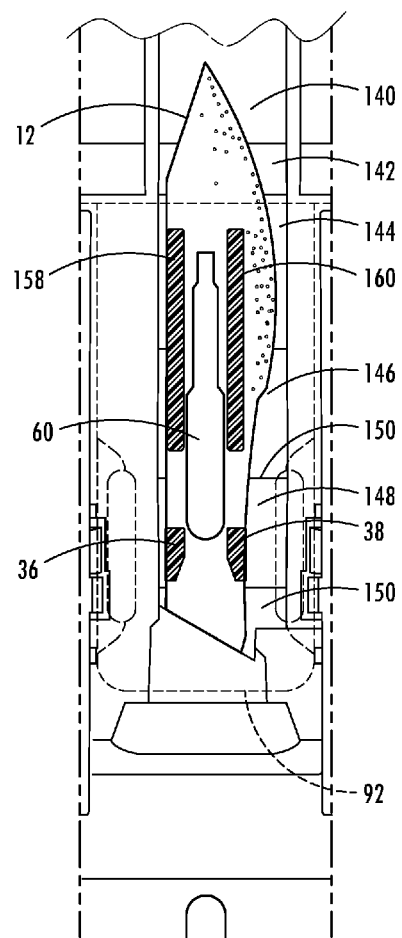
FIG. 27C is a partial front view of the scalpel handle removed from the blade disarmer and the blade disposed with the cavity with a portion of the cover member in phantom.
Figure 27D:
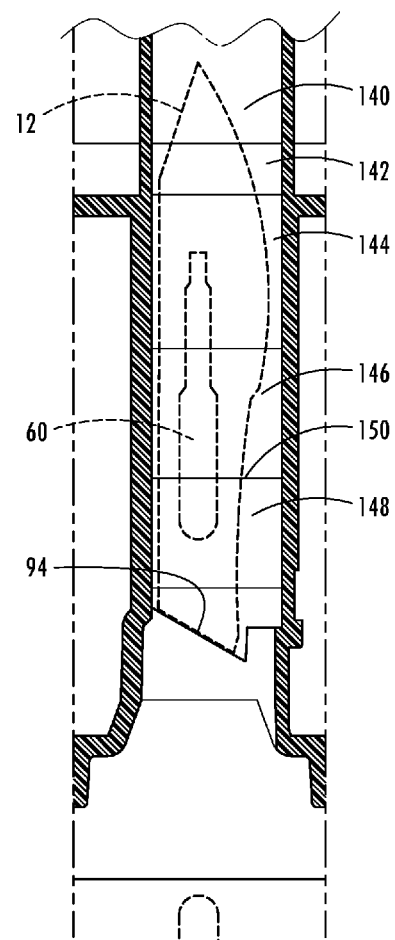
FIG. 27D is a partial front view of the scalpel handle removed from the blade disarmer and the blade disposed with the cavity with the blade and scalpel in phantom.
Figure 28:
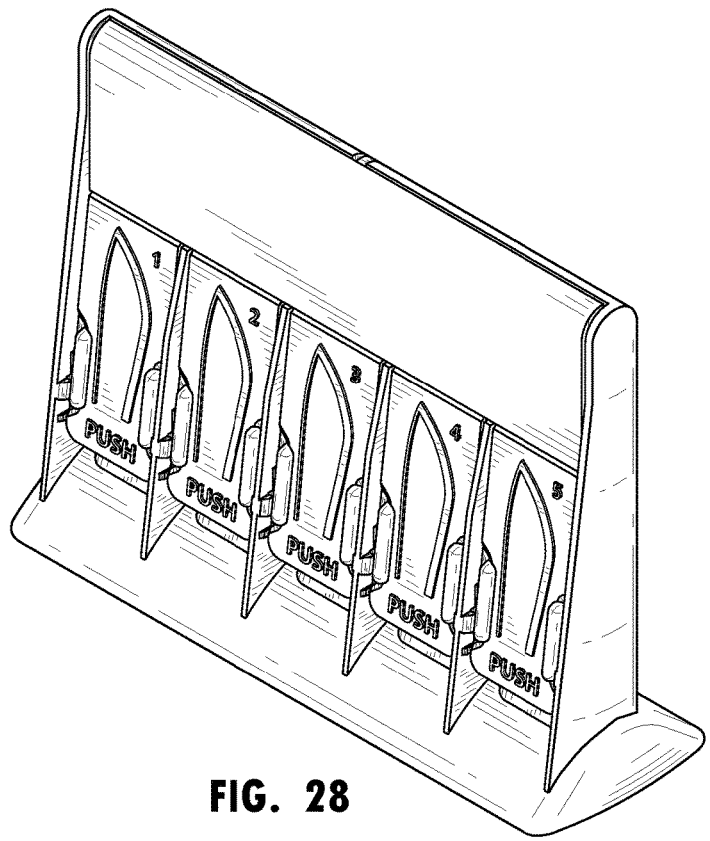
FIG. 28 is a first side elevational view of the blade disarmer of FIG. 1, according to one embodiment.
Figure 29:
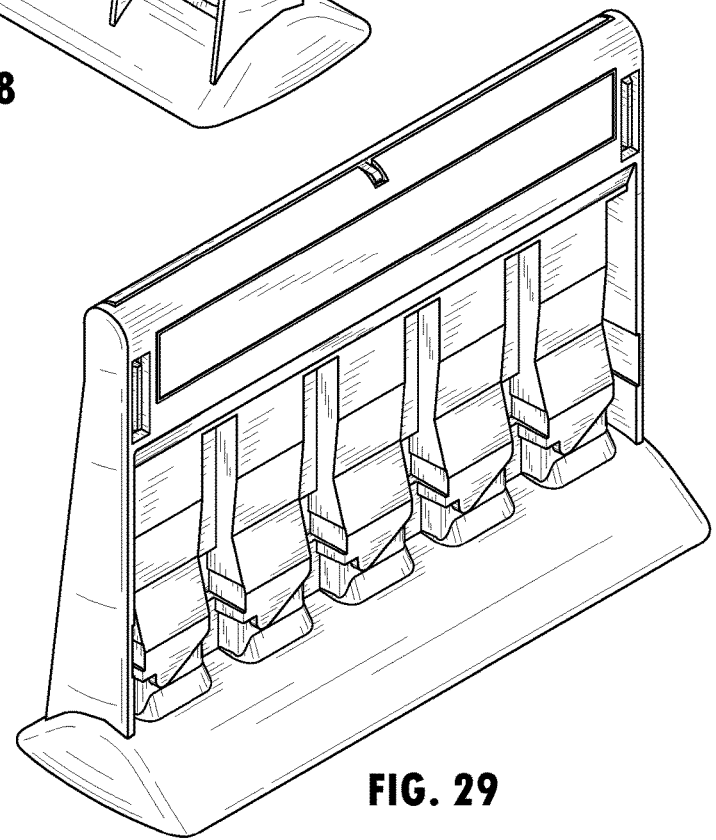
FIG. 29 is a second side elevational view of the blade disarmer of FIG. 1.
Figure 30:
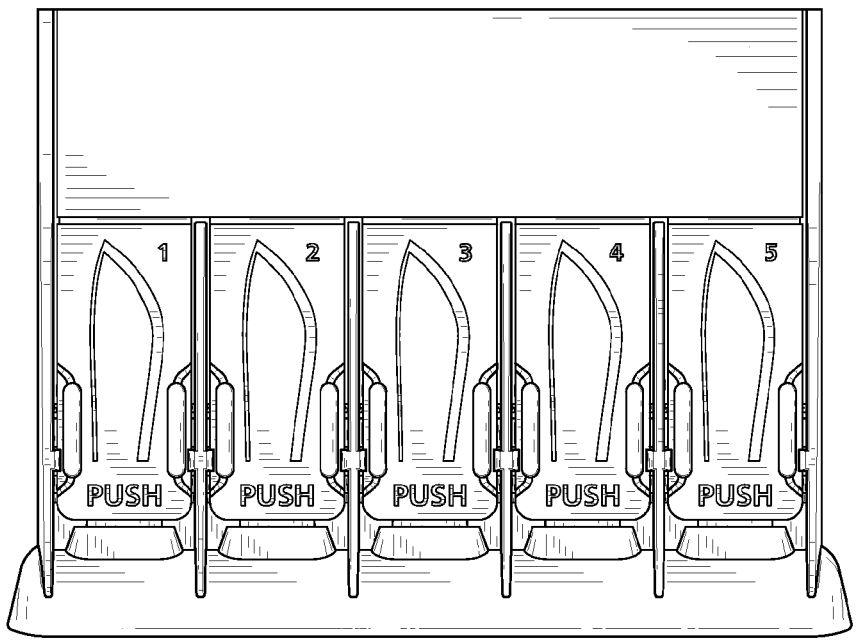
FIG. 30 is a front perspective view of the blade disarmer of FIG. 1.
Figure 31:
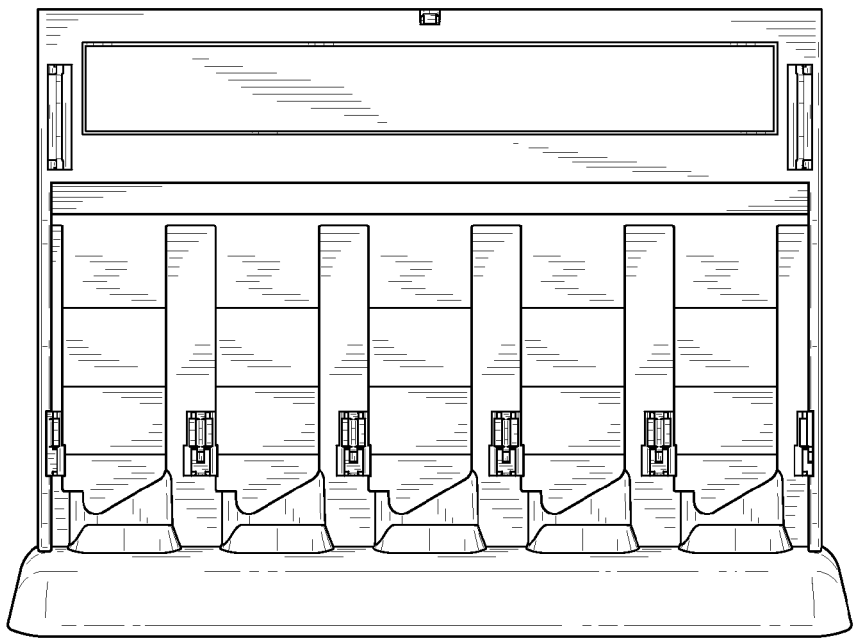
FIG. 31 is a rear perspective view of the blade disarmer of FIG. 1.
Figure 32:
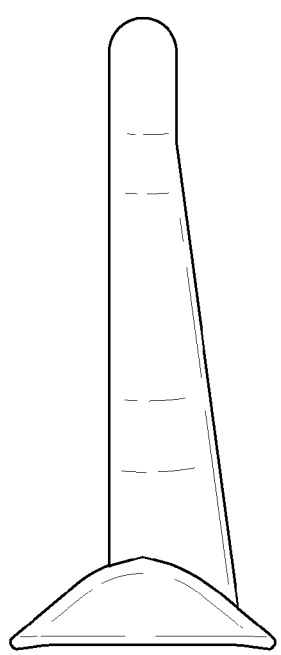
FIG. 32 is a third side elevational view of the blade disarmer of FIG. 1.
Figure 33:
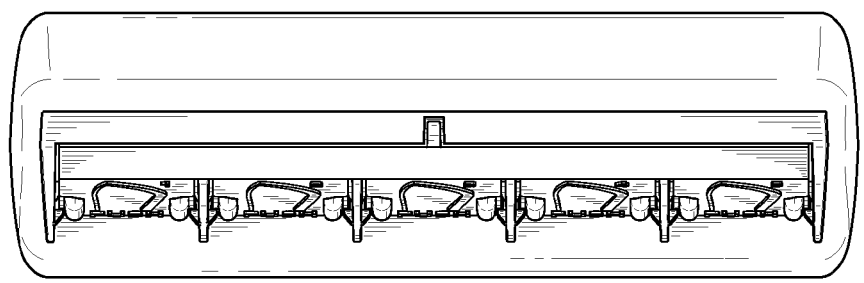
FIG. 33 is a top perspective view of the blade disarmer of FIG. 1.
Figure 34:
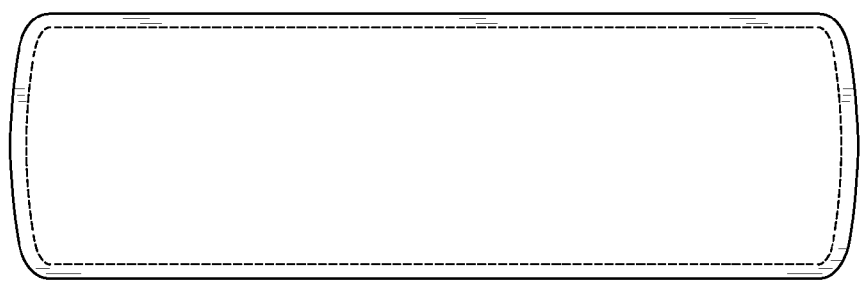
FIG. 34 is a bottom perspective view of the blade disarmer of FIG. 1.

As illustrated in FIG. 26B, the blade 12 is bent towards the base member 14. The blade mating portion 94 contacts the distal heel portion 58 of the blade 12, thereby providing upward force to assist in removal of the blade 12 from the tang 40.

The distal heel portion 58 of the scalpel blade 12 is bent so that the blade 12 is smoothly freed from the tang 40, thereby permitting that the tang 40 is extracted from the central aperture 60 of the scalpel blade 12. The blade 12 maintains contact with the blade mating portion 94 such that the blade 12 is prevented from sliding outwardly through the insertion opening 44. The scalpel handle 48 is then removed from the blade disarmer 10 free from the scalpel blade 12, which is left encapsulated within the cavity 26 of the blade disarmer 10. The scalpel handle 48 slides outwardly from the insertion opening 44, and from the scalpel blade 12, with minimal removal force. The scalpel blade 12 is tightly retained, in its bent position, within the blade disarmer 10, and will not exit the blade disarmer 10 in any orientation thereof.

As illustrated in 27-27D, once the handle 48 is removed from the blade disarmer 10 and the blade 12 is disposed within the cavity 26, the blade 12 maintains a slightly bent orientation through rearward contact with the protrusions 36, 38 and forward contact with the apex 150. Accordingly, the tab 32 is pressed forwardly by the blade 12 against the bottom portion 18 of the second, lower detent 72, thereby holding the tab 32 in a closed position. Moreover, the locking projection 90 disposed below the tab 32 substantially prevents the cavity 26 from being opened.

Referring to FIGS. 28-34, the blade disarmer 10 described and the disclosed design thereof is illustrated, according to one embodiment. The contained includes the overall appearance shown, the corresponding descriptions, any and all parts, and/or combinations thereof. As such, the right is reserved to separately claim, including by inserting a boundary around, any part, portion, element and/or combination of the disclosed design(s), and also the right is reserved to replace any solid line in any current or future line drawings with a broken line to disclaim any part, portion, element or combination thereof of the disclosed design(s) or to replace any broken line in any current or future line drawings with a solid line to claim any part, portion, element or combination thereof of the disclosed design(s). Further, any unclaimed aspects and the unclaimed descriptions set forth in this disclosure may be incorporated into the drawings and/or a design specification. It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

What is claimed is:

1. A blade disarmer, comprising:
   a base member having an elongated portion, a bottom portion, and first and second walls extending from the elongated portion;
   a cover member attached to the base member forming a cavity therebetween, wherein the cover member includes a hinge separating a body portion and a tab;
   a pair of dome-shaped portions respectively positioned over a pair openings defined by the tab;
   a closure mechanism disposed on the first and second walls and configured to maintain the tab in the plurality of positions, wherein the pair of dome-shaped portions and the pair of openings are configured to assist a pair of side surfaces of the tab proximate each respective dome-shaped portion to flex towards a center of the tab as the tab is moved between a plurality of positions and contact the closure mechanism; and
   first and second protrusions extending into the cavity configured to contact a blade within the cavity.

2. The blade disarmer of claim 1, wherein the first and second protrusions are configured to bend a distal heel portion of a blade disposed within the cavity when the tab is moved from a first position to a second position.

3. The blade disarmer of claim 2, wherein the closure mechanism is configured as a plurality of detents disposed on each respective wall that maintain the tab in a plurality of predefined positions.

4. The blade disarmer of claim 2, further comprising:
   a pair of elongated ribs extending from the cover member into the cavity, wherein the ribs are disposed between the protrusions and the hinge.

5. The blade disarmer of claim 4, wherein the elongated ribs are configured to maintain a planar orientation of a proximal cutting portion of the blade while the first and second protrusions bend a distal heel portion of the blade.

6. The blade disarmer of claim 1, further comprising:
   a plurality of intermediate walls configured to define a plurality of cavities within the blade disarmer.

7. The blade disarmer of claim 6, wherein each cavity includes an independent tab separated from the body portion by a hinge.

8. A blade disarmer, comprising:
   a base member defining an elongated portion forming an apex, a bottom portion, and a plurality of walls extending from the elongated portion;
   a cover member having a body portion removably attached to the base member forming a cavity therebetween;
   a plurality of tabs pivotably coupled to the body portion;
   a first protrusion extending from a surface of the cover member towards the base member; and
   first and second detents disposed on each of the plurality of walls, wherein the first detent is disposed at a first distance from the elongated portion and the first protrusion is disposed forwardly of the apex when the tab is disposed between the first detent and the second detent and wherein the second detent is disposed at a second distance from the elongated portion and the first protrusion is disposed rearwardly of the apex when the tab is disposed between the second detent and the base member.

9. The blade disarmer of claim 8, wherein the plurality of walls are configured to extend above a bottom portion of each of the plurality of tabs when each of the plurality of tabs are disposed between the first detent and the second detent.

10. The blade disarmer of claim 9, wherein a blade mating portion is proximate an insertion opening and within each cavity.

11. The blade disarmer of claim 10, further comprising a second protrusion extending into the cavity, wherein the first and second protrusions are configured to bend a distal heel portion of a blade disposed within the cavity.

12. The blade disarmer of claim 8, wherein the first and second detents are configured to maintain each tab in a plurality of positions including a first position wherein the cavity may be accessed, a second position wherein the cavity has a first volume, and a third position wherein the cavity has a second, smaller volume.

13. The blade disarmer of claim 8, wherein each tab defines an opening and includes a dome-shaped portion disposed over the opening that is configured to assist a side surface of the tab to move laterally towards a center of the tab as the tab is pressed over each detent.

14. The blade disarmer of claim 10, wherein the blade mating portion is configured to substantially correlate to a geometry of a shoulder portion of a scalpel.

15. A blade disarmer, comprising:
   a base member having an elongated portion, a bottom portion, and first and second walls extending from the elongated portion;
   a cover member attached to the base member forming a cavity therebetween, wherein the cover member includes a hinge separating a body portion and a tab;
   a pair of dome-shaped portions respectively positioned over a pair openings defined by the tab;
   a closure mechanism disposed on the first and second walls and configured to maintain the tab in the plurality of positions, wherein the pair of dome-shaped portions and the pair of openings are configured to assist a pair of side surfaces of the tab proximate each respective dome-shaped portion to flex towards a center of the tab as the tab is moved between a plurality of positions and contacts the closure mechanism;
   first and second protrusions extending into the cavity configured to contact a blade within the cavity, wherein the first and second protrusions are configured to bend a distal heel portion of a blade disposed within the cavity when the tab is moved from a first position to a second position; and
   a pair of elongated ribs extending from the cover member into the cavity, wherein the ribs are disposed between the protrusions and the hinge.

16. The blade disarmer of claim 15, wherein the closure mechanism is configured as a plurality of detents disposed on each respective wall that maintain the tab in a plurality of predefined positions.

17. The blade disarmer of claim 15, wherein the elongated ribs are configured to maintain a planar orientation of a proximal cutting portion of the blade while the first and second protrusions bend a distal heel portion of the blade.

18. The blade disarmer of claim 15, further comprising:
a plurality of intermediate walls configured to define a plurality of cavities within the blade disarmer.

19. The blade disarmer of claim 18, wherein each cavity includes an independent tab separated from the body portion by a hinge.

* * * * *